(12) United States Patent (10) Patent No.: US 9,147,246 B2
Friedman et al. (45) Date of Patent: Sep. 29, 2015

(54) APPARATUS AND METHOD FOR ANALYZING STREAM OF IMAGING DATA

(75) Inventors: Alon Friedman, Gedera (IL); Yoash Chassidim, Eilat (IL); Ofer Prager, Kiryat-Motzkin (IL); Ilan Shelef, Meytar (IL)

(73) Assignees: Ben-Gurion University of the Negev Research and Development Authority, Beer-Sheva (IL); Mor Research Applications Ltd., Tel-Aviv (IL)

(*) Notice: Subject to any disclaimer, the term of this patent is extended or adjusted under 35 U.S.C. 154(b) by 574 days.

(21) Appl. No.: 13/390,725

(22) PCT Filed: Sep. 1, 2009

(86) PCT No.: PCT/IL2009/000847
§ 371 (c)(1),
(2), (4) Date: Feb. 16, 2012

(87) PCT Pub. No.: WO2011/021175
PCT Pub. Date: Feb. 24, 2011

(65) Prior Publication Data
US 2012/0155735 A1 Jun. 21, 2012

Related U.S. Application Data

(60) Provisional application No. 61/272,111, filed on Aug. 18, 2009.

(51) Int. Cl.
*G06K 9/00* (2006.01)
*G06T 7/00* (2006.01)
(Continued)

(52) U.S. Cl.
CPC ............ *G06T 7/0016* (2013.01); *A61B 5/0275* (2013.01); *A61B 6/037* (2013.01); *A61B 6/5217* (2013.01); *A61B 8/5223* (2013.01); *G01R 33/5635* (2013.01); *A61B 3/0025* (2013.01); *A61B 3/1241* (2013.01); *A61B 5/0059* (2013.01); *A61B 5/0263* (2013.01); *A61B 5/7207* (2013.01); *A61B 6/501* (2013.01); *A61B 6/507* (2013.01); *A61B 8/06* (2013.01); *G01R 33/563* (2013.01);
(Continued)

(58) Field of Classification Search
None
See application file for complete search history.

(56) References Cited

U.S. PATENT DOCUMENTS

2008/0125648 A1* 5/2008 Bi et al. .......................... 600/425
2010/0198054 A1* 8/2010 Ewing et al. ................... 600/420
(Continued)

FOREIGN PATENT DOCUMENTS

WO    WO 2011/021175    2/2011

OTHER PUBLICATIONS

International Preliminary Report on Patentability Dated Mar. 1, 2012 From the International Bureau of WIPO Re. Application No. PCT/IL2009/000847.
(Continued)

*Primary Examiner* — Tahmina Ansai

(57) ABSTRACT

A method of analyzing a stream of imaging data is disclosed. The method comprises: for each picture-element of the data, associating a vector of features indicative of temporal intensity variation relative to baseline intensity, thereby providing a plurality of vectors. The method further comprises clustering the picture-elements according to the vectors, thereby providing a plurality of clusters, and identifying different compartments in the vasculature based on the clusters.

39 Claims, 11 Drawing Sheets
(9 of 11 Drawing Sheet(s) Filed in Color)

(51) Int. Cl.

| | | |
|---|---|---|
| A61B 5/0275 | (2006.01) | |
| A61B 6/03 | (2006.01) | |
| A61B 8/08 | (2006.01) | |
| A61B 3/00 | (2006.01) | |
| A61B 3/12 | (2006.01) | |
| A61B 5/00 | (2006.01) | |
| A61B 5/026 | (2006.01) | |
| A61B 6/00 | (2006.01) | |
| A61B 8/06 | (2006.01) | |
| G01R 33/56 | (2006.01) | |
| G01R 33/563 | (2006.01) | |

(52) U.S. Cl.
CPC ... *G01R 33/5608* (2013.01); *G06T 2207/10064* (2013.01); *G06T 2207/10096* (2013.01); *G06T 2207/30016* (2013.01); *G06T 2207/30041* (2013.01); *G06T 2207/30104* (2013.01)

(56) References Cited

U.S. PATENT DOCUMENTS

2011/0293157 A1* 12/2011 Ye et al. .................. 382/131
2012/0155735 A1* 6/2012 Friedman et al. ........... 382/131

OTHER PUBLICATIONS

Communication Pursuant to Article 94(3) EPC Dated May 14, 2013 From the European Patent Office Re. Application No. 09787554.6.
Summons to Attend Oral Proceedings Pursuant to Rule 115(1) EPC Dated Feb. 6, 2014 From the European Patent Office Re. Application No. 09787554.6.
"Dynamic in Vivo Imaging of Cerebral Blood Flow and Blood-Brain Barrier Permeability", NeuroImage 49: 337-344, 2010.
International Search Report and the Written Opinion Dated May 13, 2011 From the International Searching Authority Re. Application No. PCT/IL2009/000847.
Bisdas et al. "Delineation and Segmentation of Cerebral Tumors by Mapping Blood-Brain Barrier Disruption With Dynamic Contrast-enhanced CT and Tracer Kinetics Modeling—A Feasibility Study", European Radiology, XP019587893, 18(1): 143-151, Aug. 14, 2007. Abstract, Introduction.
Boss et al. "Post-Radiotherapy Contrast Enhancement Changes in Fast Dynamic MRI of Cervical Carcinoma", Journal of Magnetic Resonance Imaging, XP002628841, 13(4): 600-606, Apr. 2001. Abstract, Figs. 1, 2, Section "Data Analysis".
Guizar-Sicairos et al. "Efficient Subpixel Image Registration Algorithms", Optics Letters, 33: 156-158, 2008.
Hartigan et al. "Algorithm AS 136: A K-Means Clustering Algorithm", Journal of the Royal Statistical Society. Series C (Applied Statistics), 28: 100-108, 1979.
Henninger et al. "Stimulating Circle of Willis Nerve Fibers Preserves the Diffusion-Perfusion Mismatch in Experimental Stroke", Stroke, 38: 2779-2786, 2007.
Jackson "Analysis of Dynamic Contrast Enhanced MRI", The British Journal of Radiology, XP002628839, 77(Spec.2): S154-S166, 2004. Abstract, Section "Analysis of DSC-MRI Data—Basic Theory", Figs.2, 3.
Keys "Cubic Convolution Interpolation for Digital Image Processing", IEEE Transactions on Acoustics, Speech and Signal Processing, 29: 1153-1160, 1981.
Moate et al. "A Modified Logistic Model to Describe Gadolinium Kinetics in Breast Tumors", Magnetic Resonance Imaging, XP002628840, 22(4): 467-473, May 2004. Abstract, Section 1, 2.
Prager et al. "Dynamic in Vivo Imaging of Cerebral Blood Flow and Blood-Brain Barrier Permeability", Neuroimage, XP026851232, 49(1): 337-344, Aug. 12, 2009.
Rempp et al. "Quanttification of Regional Cerebral Blood Flow and Volume With Dynamic Susceptibility Contrast-Enhanced MR Imaging", Radiology, XP001084696, 193(3): 637-641, Dec. 1, 1994. Abstract, Section "Data Analysis".
Woitzik et al. Cortical Perfusion Measurement by Indocyanine-Green Videoangiography in Patients Undergoing Hemicraniectomy for Malignant Stroke, Stroke, 37: 1549-1551, 2006.
Seiffert et al. "Lasting Blood-Brain Barrier Disruption Induces Epileptic Focus in the Rat Somatosensory Cortex", The Journal of Neuroscience, 24: 7829-7836, 2004.

\* cited by examiner

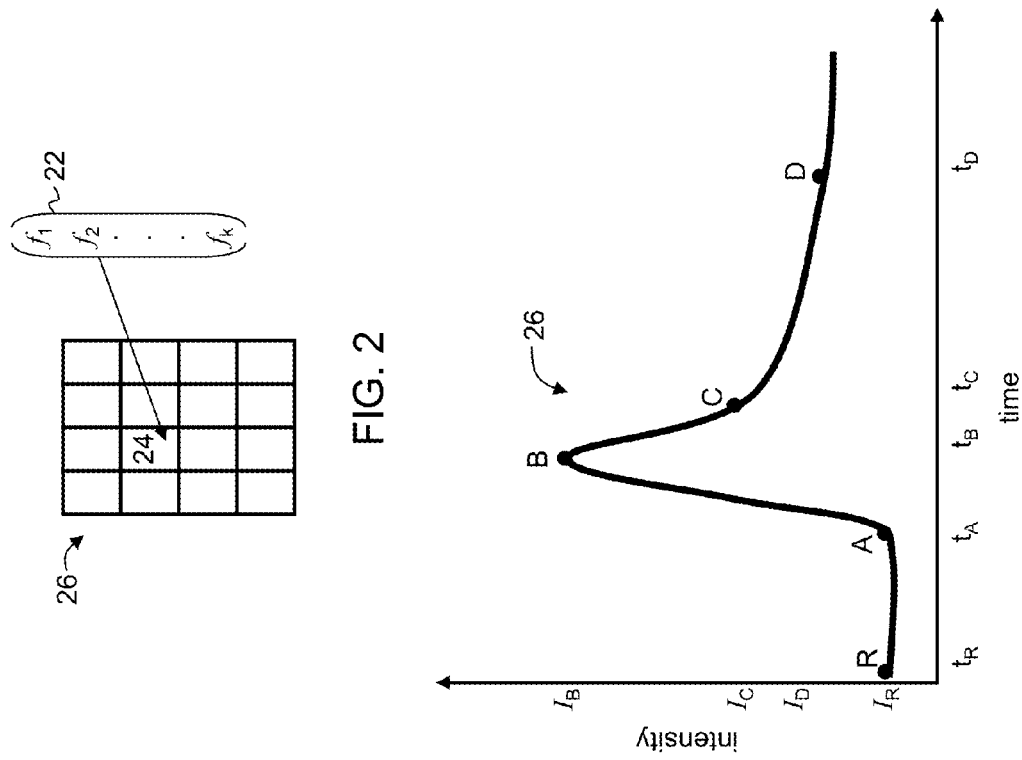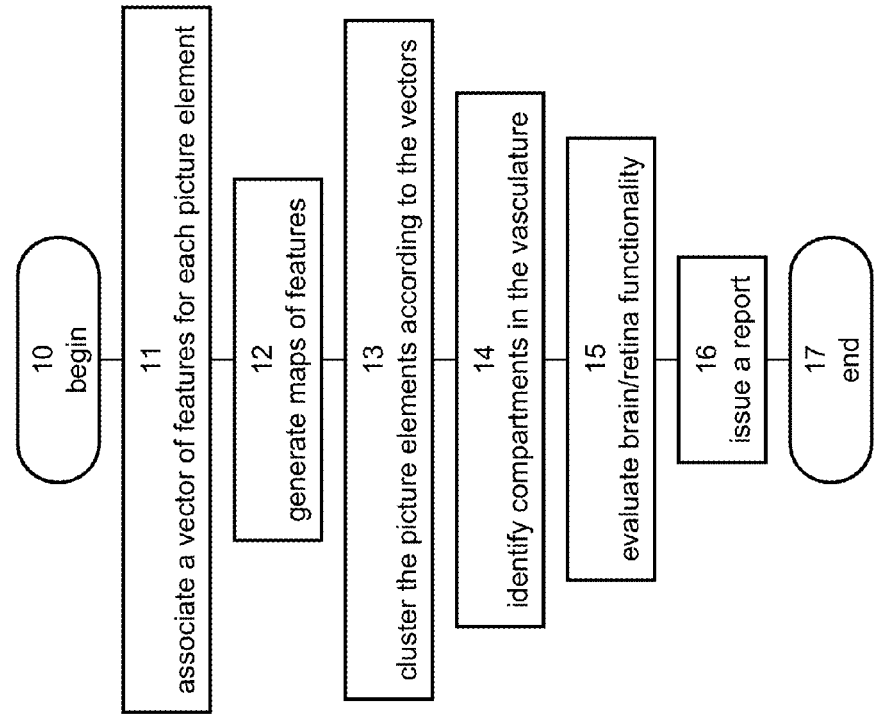

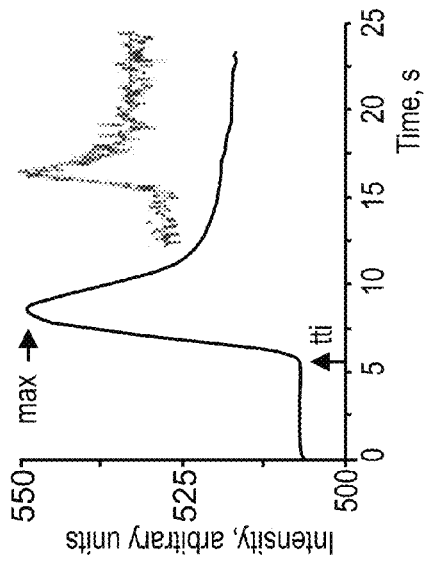
FIG. 6B
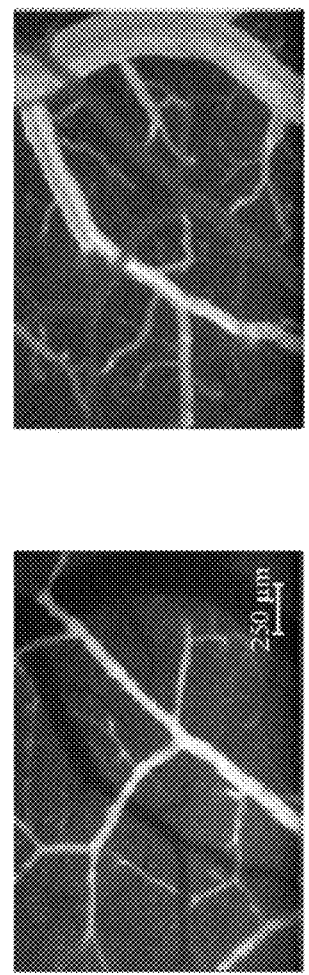
FIG. 6A
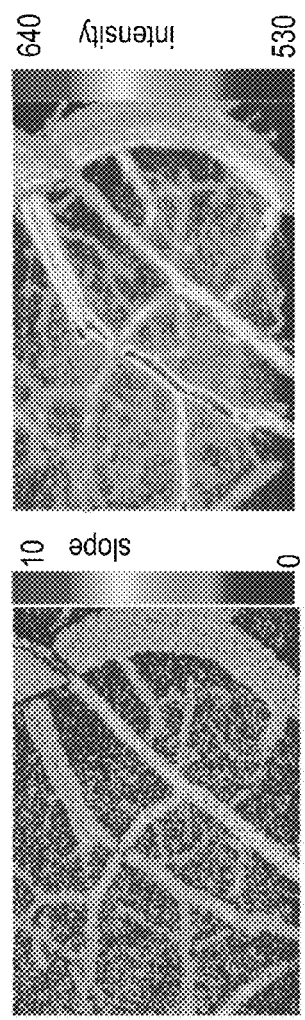
FIG. 6C
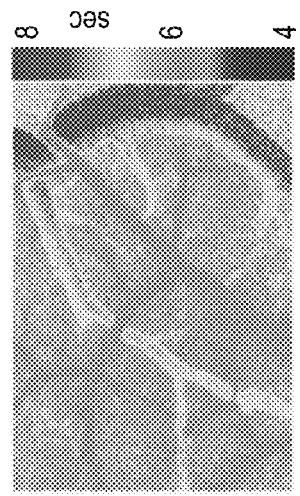
FIG. 6F
FIG. 6E
FIG. 6D

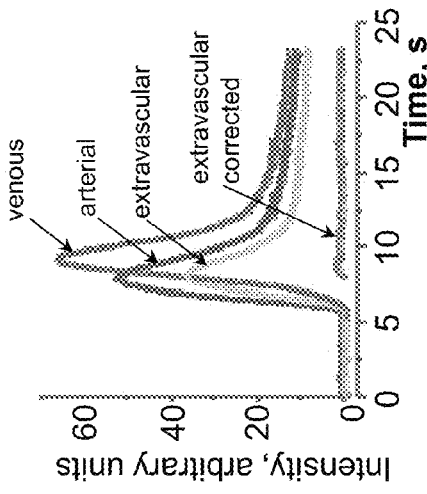
FIG. 6-I
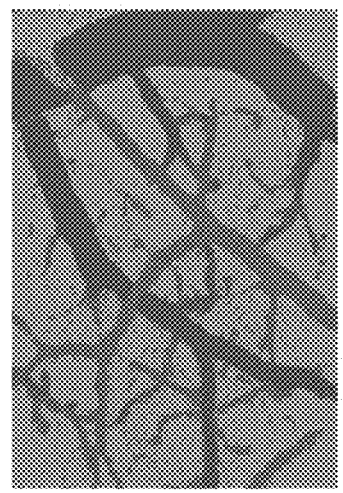
FIG. 6H
FIG. 6G
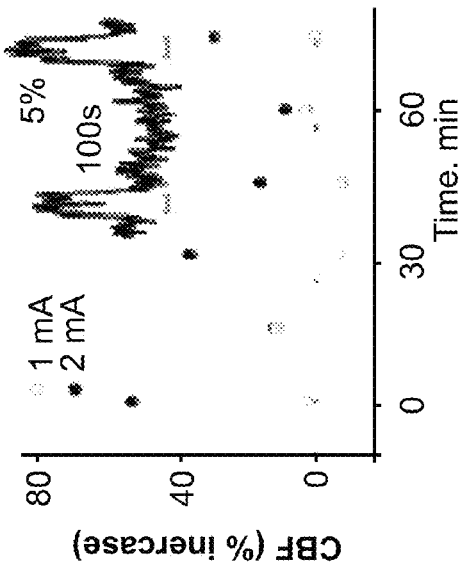
FIG. 7C
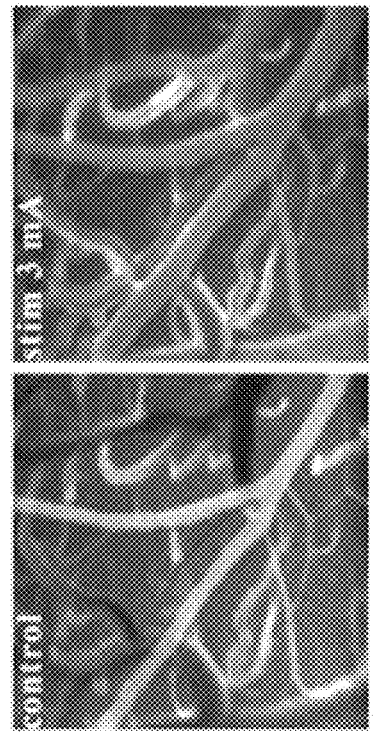
FIG. 7B
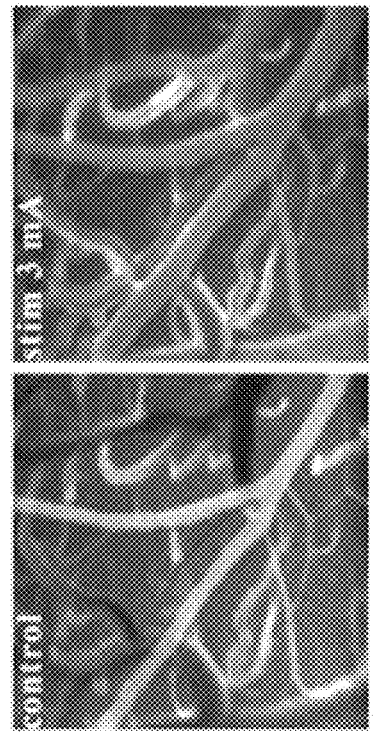
FIG. 7A

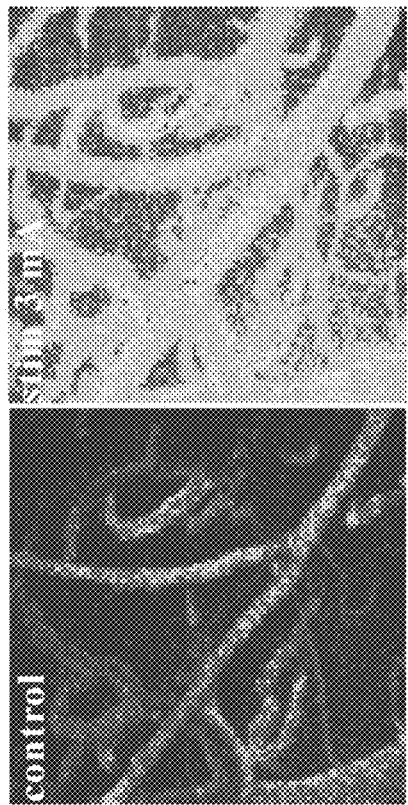
FIG. 7F
FIG. 7E
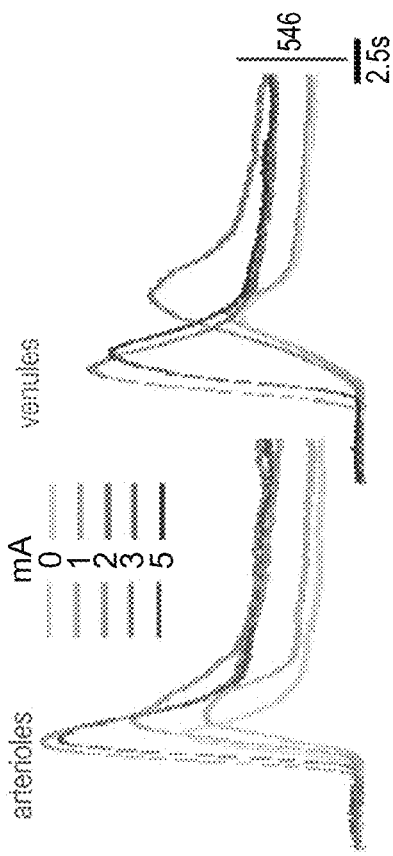
FIG. 7H
FIG. 7G
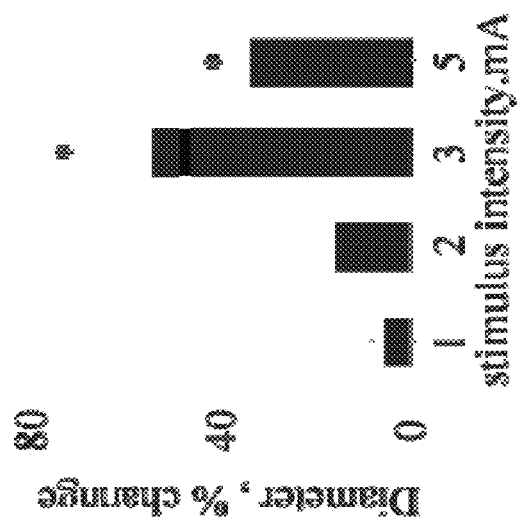
FIG. 7D

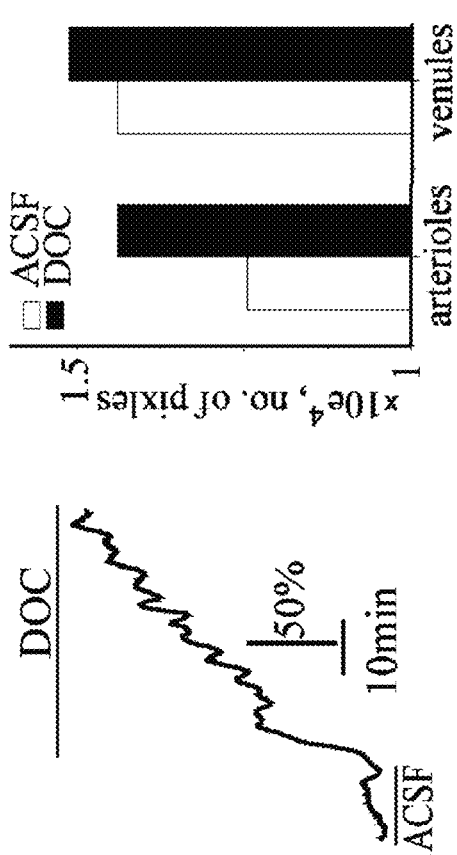
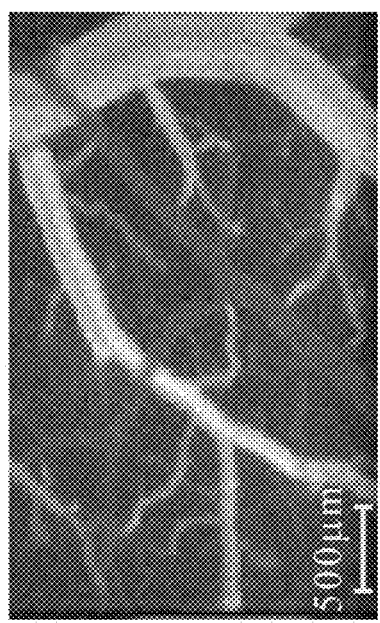
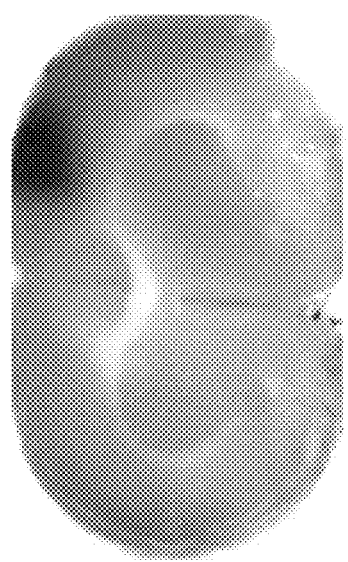
FIG. 8A  FIG. 8B  FIG. 8C  FIG. 8D  FIG. 8E

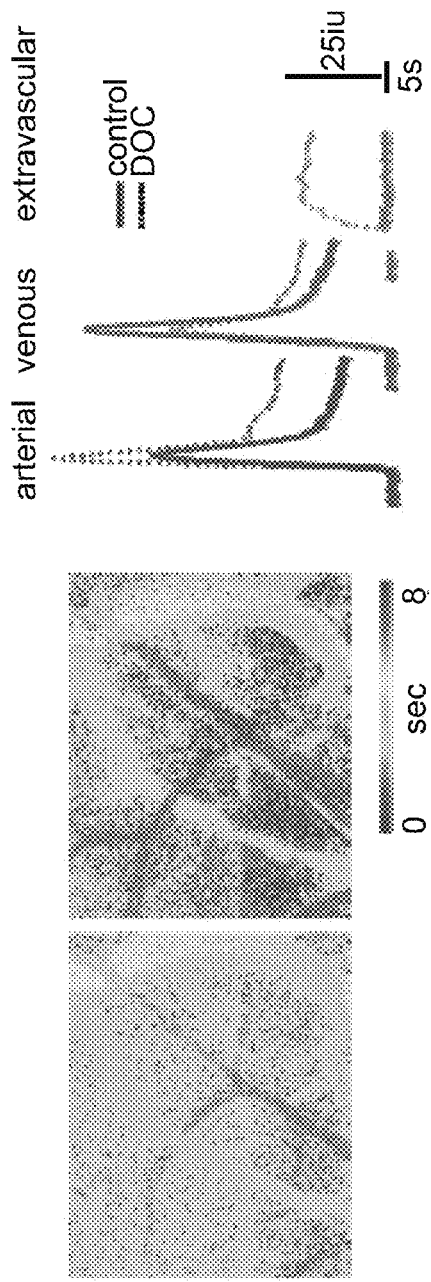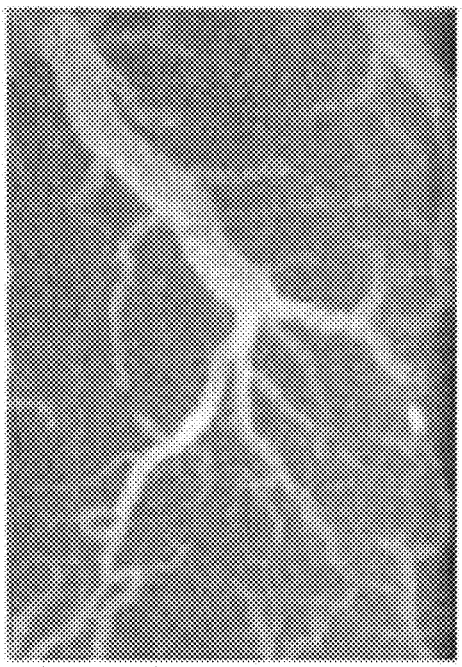

FIG. 9G    FIG. 9H
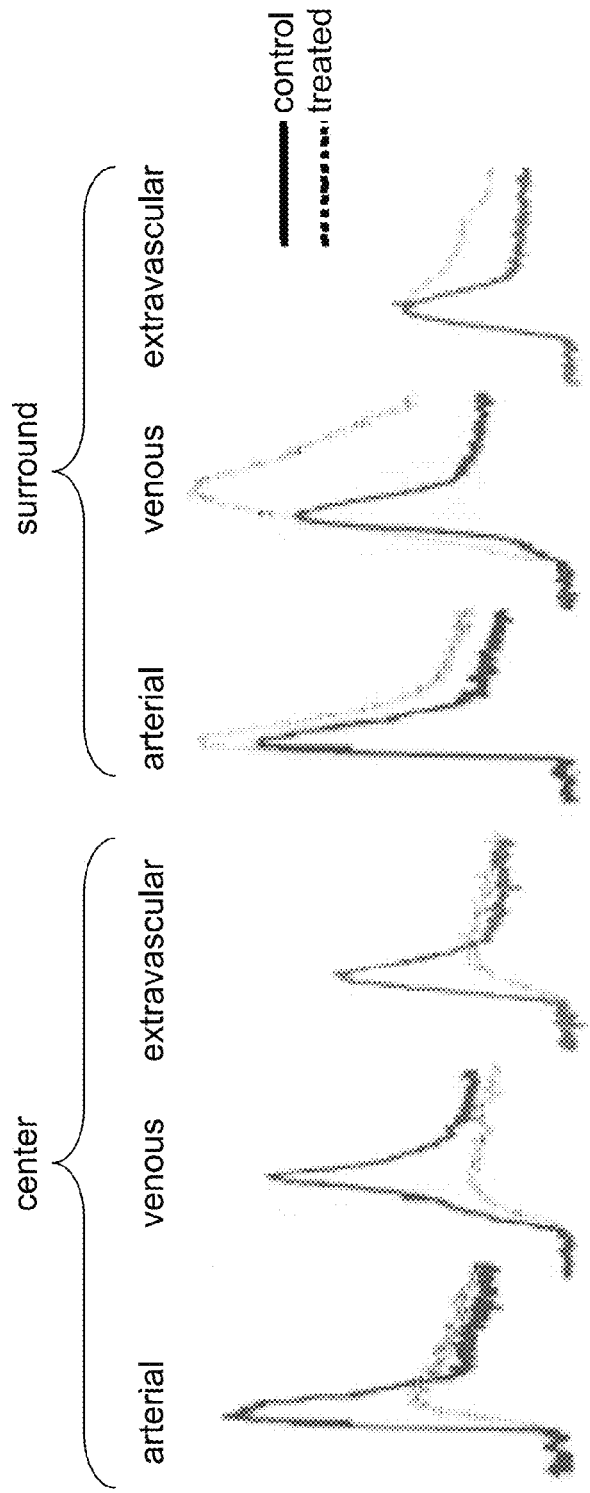
FIG. 9-I

APPARATUS AND METHOD FOR ANALYZING STREAM OF IMAGING DATA

RELATED APPLICATIONS

This application is a National Phase of PCT Patent Application No. PCT/IL2009/000847 having International filing date of Sep. 1, 2009, which claims the benefit of priority of U.S. Provisional Patent Application No. 61/272,111 filed on Aug. 18, 2009. The contents of the above applications are all incorporated herein by reference.

FIELD AND BACKGROUND OF THE INVENTION

The present invention, in some embodiments thereof, relates to image analysis and processing and, more particularly, but not exclusively, to analysis of imaging data pertaining to blood flow.

For human sense and movement, homeostasis and various higher functions such as emotion, memory, language and thinking, there are often control mechanisms for each specific site or region in the brain. Such localization of functions in the brain had been confirmed by observing changes in behavior of patients suffering from regional damage to the brain caused by trauma or cerebral blood vessel impediment, or states of epileptic attack, and by estimating the function of the damaged region.

Brain metabolism and function are attributed to the neurovascular unit. This unit comprises the cerebral circulation, including the pial and intraparenchymal cerebral blood vessels with their extrinsic and intrinsic innervation, perivascular pericytes, astrocytes and surrounding neurons. The regional cerebral blood flow (rCBF) is related to neuronal activity and metabolic demand, also known as "neurovascular coupling". In addition, the rCBF is autoregulated and can therefore remain constant over a wide range of perfusion pressures. In pathological brain conditions associated with vascular abnormalities (e.g., stroke) and primary neuronal dysfunctions (e.g., epileptic seizure and cortical spreading depression), regulation of the rCBF is often impaired. For example, under subarachnoid hemorrhage and traumatic brain injury, neurovascular coupling may be breached, leading to exacerbation of ischemic neuronal damage.

Until recent years, assessment of the cerebrovascular status in intensive care unit (ICU) patients has been confined to the determination of cerebral perfusion pressure using intracranial pressure measurements. New techniques for cerebrovascular assessments include thermal diffusion flowmetry, which has been used in the ICU owing to the availability of a new generation of intracranial probes. The probe provides regional cerebral blood flow (rCBF) data in absolute units (e.g., ml/100 g/min). Several types of such probes are described, for example, in U.S. Pat. Nos. 4,354,504, 4,677, 985 and 5,207,227.

Another technology is transcranial Doppler velocimetry in which instruments are equipped with continuous monitoring probes that measure the velocity of blood flow in large intracranial conductance vessels. This technology is described, for example, in U.S. Pat. Nos. 5,379,770, 6,390,979 and 6,468, 219.

An additional technology which is used for measuring CBF is laser Doppler flowmetry which measures the movement of red blood cells within the microcirculation using Doppler shifts undergone by coherent radiation generated by lasers. Typically, a fiberoptic probe structure is placed in contact with the tissue and guides incident light from the laser source to the tissue, as well as back-scattered light from the tissue to a photodetector within a flowmeter instrument. The flowmeter instrument processes the photodetector signal to elaborate a continuous voltage signal versus time which is linearly proportional to the real blood flow. Laser doppler based techniques are described in, e.g., U.S. Pat. Nos. 5,579, 774 and 5,916,171.

Also known are various brain tissue imaging techniques such as computer tomography (CT), positron emmision tomography (PET) and magnetic resonance imaging (MRI) which allow diagnosing focal regions by imaging.

A mechanism that that protects the brain from fluctuations in blood chemistry is known as "Blood-Brain Barrier" (BBB). The BBB is a complex structural and functional barrier for the maintenance of the normal environment for nerve cells in the central nervous system. Brain endothelial cells are different from those found in other tissues of the body. In particular, they form complex tight junctions between themselves. Function of the BBB depends on these tight intercellular junctions which, together with other components of the barrier, form a continuous "wall" against the passive movement of many molecules from the blood to the brain. Endothelial cells within the central nervous system (CNS) also display fewer pinocytotic vesicles, which in other tissues allow somewhat unselective transport across the capillary wall. In addition, continuous gaps or channels running through the cells, which would allow unrestrained passage, are absent. Yet, this isolation of the brain from the bloodstream is not complete, since an exchange of nutrients and waste products does exist. The presence of specific transport systems within the capillary endothelial cells assures that the brain receives, in a controlled manner, all of the compounds required for normal growth and function.

The unique biological aspect of the BBB is oftentimes addressed in the context of treatment of CNS disorders. The BBB serves as the main obstacle for the delivery of drugs into the brain by either preventing their entrance or facilitating transport from the brain back to the circulation once they crossed, by drug transport proteins, probably contributing to drug resistance in some cases (e.g., epilepsy). In addition, BBB breakdown has been reported in almost all CNS disorders including brain tumors, ischemic events, tumors, brain tumors, multiple sclerosis and neurodegenerative disorders (e.g., Alzheimer's disease).

In recent years it is recognized that BBB breakdown may lead directly to malfunction of the neurovascular unit and hence to long-lasting changes in neuronal activity, followed by neuronal loss.

Over the years, extensive research has been made in the BBB field. Attempts have made to develop agents capable of crossing the BBB (see, e.g., U.S. Pat. Nos. 4,801,575, 5,004, 697, 6,419,949 and 6,294,520), agents which increase BBB permeability (see, e.g., U.S. Pat. Nos. 5,434,137, 5,506,206 and 5,591,715), and various techniques for delivering substances across the BBB (see, e.g., U.S. Pat. Nos. 5,670,477, 5,752,515 and 6,703,381), treating a damaged BBB (see, e.g., U.S. Pat. No. 4,439,451), analyzing the BBB (see, e.g., U.S. Pat. No. 6,574,501), and the like. Numerous attempts have also been made to develop techniques for testing the ability of substances to cross the BBB. To this end see, e.g., U.S. Pat. No. 5,266,480.

SUMMARY OF THE INVENTION

According to an aspect of some embodiments of the present invention there is provided a method of analyzing a stream of imaging data arranged gridwise in a plurality of picture-elements associated with intensity values pertaining to a level of a detectable tracer in the vasculature of a living subject. The method comprises: for each picture-element, associating a vector of features indicative of temporal intensity variation relative to a baseline intensity, thereby providing a plurality of vectors. The method further comprises clustering the picture-elements according to the vectors, thereby providing a plurality of clusters, and identifying different compartments in the vasculature based on the clusters.

According to an aspect of some embodiments of the present invention there is provided a method of imaging an organ of a living subject having a detectable tracer in the vasculature. The method comprises imaging the organ to provide a stream of imaging data, and analyzing a stream of imaging data by the analysis method described herein.

According to some embodiments of the invention the imaging comprises fluorescence imaging.

According to some embodiments of the invention the imaging comprises computerized tomography.

According to some embodiments of the invention the imaging comprises magnetic resonance imaging.

According to some embodiments of the invention the method further comprises identifying at least one extravascular compartment based on the clusters.

According to some embodiments of the invention the method further comprises generating a map of at least one of the features over the grid.

According to some embodiments of the invention the imaging data pertain to a retina of the subject.

According to some embodiments of the invention the method further comprises evaluating retinal functionality based on the clusters.

According to some embodiments of the invention the imaging data pertain to the brain of the subject.

According to some embodiments of the invention the method further comprises evaluating brain functionality based on the clusters.

According to an aspect of some embodiments of the present invention there is provided apparatus for analyzing a stream of imaging data arranged gridwise in a plurality of picture-elements associated with intensity values pertaining to a level of a detectable tracer in the vasculature of a living subject. The apparatus comprises: a vector associating unit, for associating, for each picture-element, a vector of features indicative of temporal intensity variation relative to a baseline intensity, thereby to provide a plurality of vectors. The apparatus further comprises a clustering unit, for clustering the picture-elements according to the vectors, thereby to provide a plurality of clusters; and an identification unit, for identifying different compartments in the vasculature based on the clusters.

According to an aspect of some embodiments of the present invention there is provided an imaging apparatus which comprises an imaging device and an analysis apparatus which comprises a vector associating unit, a clustering unit and an identification unit as described herein.

According to some embodiments of the invention the identification unit is configured for identifying at least one extravascular compartment based on the clusters.

According to some embodiments of the invention the apparatus further comprises a mapping unit for generating a map of at least one of the features over the grid.

According to some embodiments of the invention the apparatus further comprises an evaluator for evaluating retinal and/or brain functionality based on the clusters.

According to some embodiments of the invention the retinal functionality comprises blood retinal barrier permeability. According to some embodiments of the invention the retinal functionality comprises retinal artery occlusion.

According to some embodiments of the invention the brain functionality comprises regional cerebral blood flow. According to some embodiments of the invention the brain functionality comprises vasodilatation. According to some embodiments of the invention the brain functionality comprises blood brain barrier permeability.

According to some embodiments of the invention the features comprise time-intervals measured from a reference time to a time at which the intensity exhibits a functional transition.

According to some embodiments of the invention the features comprise a time-interval defined from a time at which the tracer is introduced into the vasculature to a time at which intensity of the picture-element rises above the baseline intensity.

According to some embodiments of the invention the features comprise a time-interval over which the intensity of the picture-element is enhanced relative to the baseline intensity.

According to some embodiments of the invention the features comprise a time-interval defined from a time at which the tracer is introduced into the vasculature to a time at which intensity of the picture-element reaches a local maximum.

According to some embodiments of the invention the features comprise a combination of at least two time-intervals selected from the group consisting of: a time-interval defined from a time at which the tracer is introduced into the vasculature to a time at which intensity of the picture-element rises above the baseline intensity; a time-interval over which the intensity of the picture-element is enhanced relative to the baseline intensity; and a time-interval defined from the time at which the tracer is introduced into the vasculature to a time at which intensity of the picture-element reaches a local maximum.

According to some embodiments of the invention the features comprise a maximal intensity value over a time-interval over which the intensity of the picture-element is enhanced relative to the baseline intensity.

According to some embodiments of the invention the features comprise at least one slope characterizing rate of change in intensity of the picture-element.

According to some embodiments of the invention the features comprise a time-interval defined from a time at which the tracer is introduced into the vasculature to a time at which intensity of the picture-element rises above the baseline intensity, and wherein the picture-element is classified as arteriole or venule based the time-interval and respective time-intervals of nearby picture-elements.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram describing a method suitable for analyzing a stream of imaging data according to various exemplary embodiments of the present invention;

FIG. 2 is a schematic illustration of a grid of picture-elements and a vector of features, according to various exemplary embodiments of the present invention;

FIG. 3 is a schematic illustration of an exemplified intensity-time curve.

FIG. 4 is flowchart diagram describing a method suitable for imaging an organ of a living subject having a detectable tracer in the vasculature, according to various exemplary embodiments of the present invention.

FIG. 5 is a schematic illustration of an apparatus for analyzing a stream of imaging data, according to various exemplary embodiments of the present invention;

Figure 11A:
Figure 10:
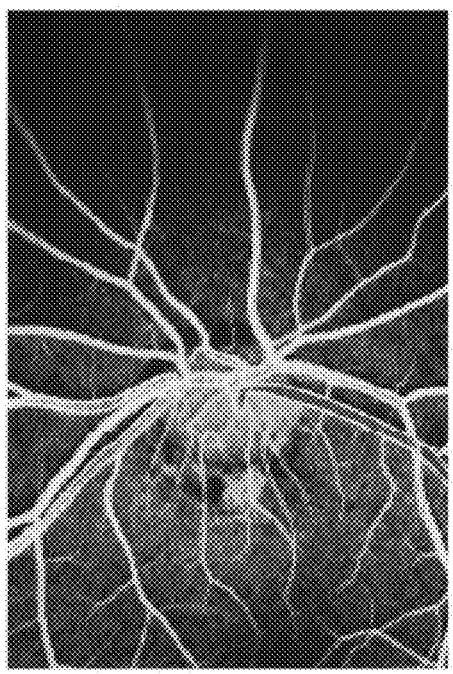
Figure 11B:
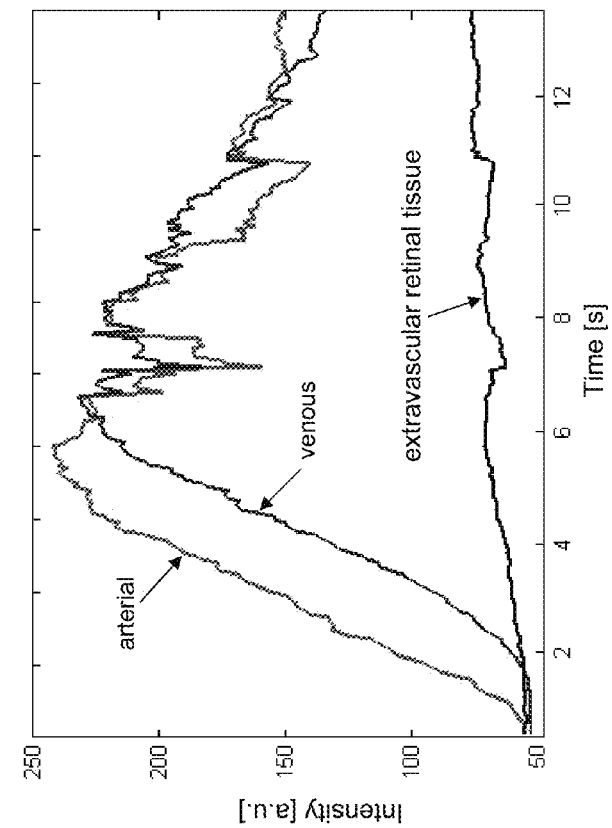
Figure 12C:
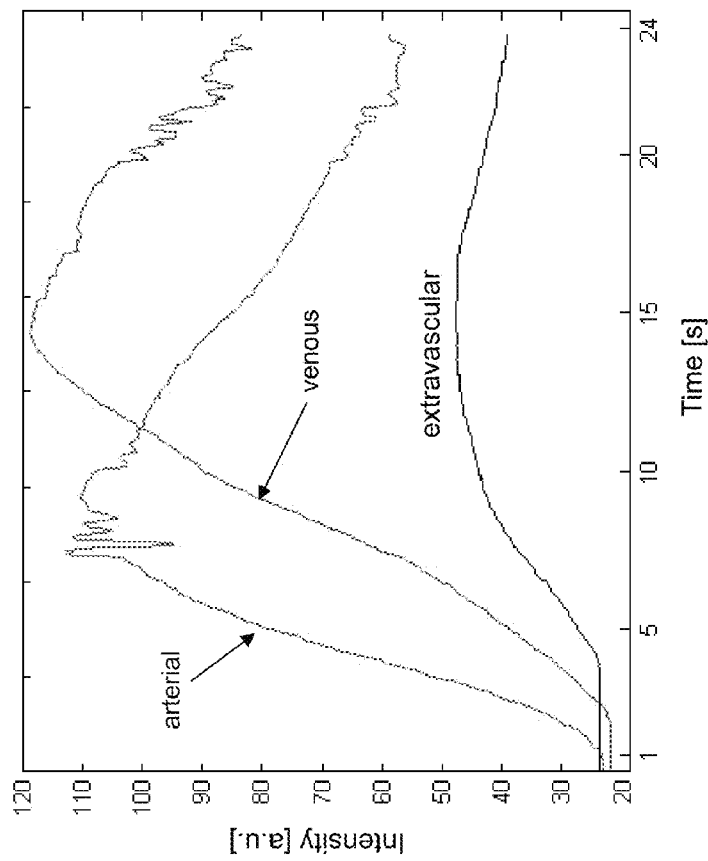
Figure 12A:
Figure 12B:
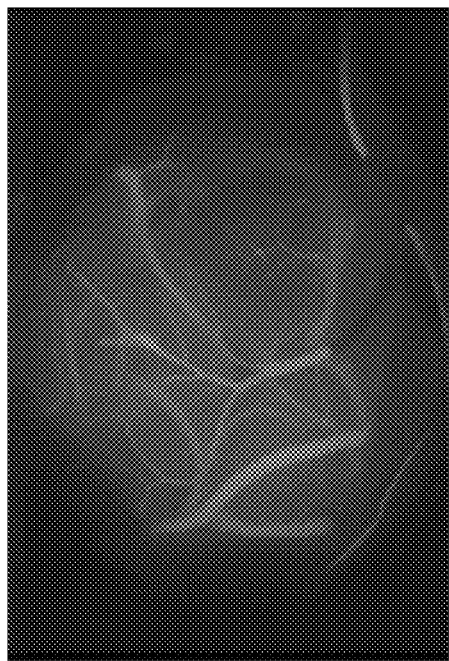

FIGS. 6A-I show results of experiments performed in accordance with some embodiments of the present invention for visualizing flow in pial vessels;

FIGS. 7A-H show results of experiments performed in accordance with some embodiments of the present invention for imaging of increased rCBF;

FIGS. 8A-H show results of experiments performed in accordance with some embodiments of the present invention for imaging for analysis of BBB permeability;

FIGS. 9A-I show results of experiments performed in accordance with some embodiments of the present invention for imaging of blood flow in focal ischemia;

FIG. 10 is a fluorescence image of a retina captured during experiment performed in accordance with preferred embodiments of the present invention;

FIGS. 11A and 11B show results of cluster analysis performed in accordance with some embodiments of the present invention for identifying different vasculature compartments in a retina;

FIGS. 12A and 12B are human brain images captured during a neurosurgical procedure;

FIG. 12C shows results of cluster analysis performed in accordance with some embodiments of the present invention for identifying different vasculature compartments in a human brain.

DESCRIPTION OF SPECIFIC EMBODIMENTS OF THE INVENTION

The present invention, in some embodiments thereof, relates to image analysis and processing and, more particularly, but not exclusively, to analysis of imaging data pertaining to blood flow in blood vessels such as, but not limited to, small blood vessels (e.g., arterioles and venules). Some embodiments of the present invention relate to imaging and, more particularly, but not exclusively, to blood flow imaging.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some embodiments of the present invention provide a method suitable for analyzing a stream of imaging data according to various exemplary embodiments of the present invention.

The method can be embodied in many forms. For example, it can be embodied in on a tangible medium such as a computer for performing the method steps. It can be embodied on a computer readable medium, comprising computer readable instructions for carrying out the operations of the method. In can also be embodied in electronic device having digital computer capabilities arranged to run the computer program on the tangible medium or execute the instruction on a computer readable medium.

Computer programs implementing the method can commonly be distributed to users on a distribution medium such as, but not limited to, a floppy disk, CD-ROM and non-volatile memory devices. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments analyses of a stream of imaging data arranged gridwise in a plurality of picture-elements (e.g., pixels, group of pixels, etc.).

The term "pixel" is sometimes abbreviated herein to indicate a picture-element. However, this is not intended to limit the meaning of the term "picture-element" which refers to a unit of the composition of an image.

The stream of imaging data can be in the form of a series of images or a series of batches of images captured at a rate which is selected so as to provide sufficient information to allow spatial as well as time-dependent analysis as further detailed hereinbelow. For example, the images can be acquired by a video camera. The picture-elements of the images are associated with intensity values.

Ideally, the input to the method is the amount of light at each point of a scene. This ideal input is rarely attainable in practical systems. Therefore, the scope of the present embodiments includes the processing of a sampled version of the scene. Specifically, the input to the method of the present embodiments is digital signals resolvable to discrete intensity values at each picture element over the grid. Thus, the grid samples the scene, and the discrete intensity values sample the amount of light. The update rate of images in the stream provides an additional sampling in the time domain.

References to an "image" herein are, inter alia, references to values at picture elements, treated collectively, as an array. Thus, the term "image" as used herein also encompasses a mathematical object which does not necessarily correspond to a physical object. The original and processed images certainly do correspond to a physical object which is scene from which the imaging data are acquired.

The scene is preferably an organ of a living subject having a vasculature. For example, the scene can be the brain or a retina of the subject.

The intensity values of the picture-elements pertain to a level of a detectable tracer in the vasculature of the subject. For example, the images can be acquired by florescence imaging, computerized tomography (CT) and magnetic resonance imaging (MRI).

When the images are acquired by florescence imaging, the detectable tracer is a fluorescent dye that can be introduced into the vasculature of the subject prior to or during the imaging.

Fluorescent dyes suitable for the present embodiments include, without limitation Indocyanine green, 3-Hydroxypyrene 5,8,10-Tri Sulfonic acid, 5-Hydroxy Tryptamine, 5-Hydroxy Tryptamine (5-HT), Acid Fuchsin, Acridine Orange, Acridine Red, Acridine Yellow, Acriflavin, AFA (Acriflavin Feulgen SITSA), Alizarin Complexon, Alizarin Red, Allophycocyanin, ACMA, 4-dicyano-methylene-2-methyl-6-(p-dimethylaminostyryl)4H-pyran, fluorescent chelates of lanthanide ions, for example ions of Terbium, Samarium, and, Europium, Aminoactinomycin D, Aminocoumarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy F1, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Cate cholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NHCH3, DAPI, Diamino Phenyl Oxydiazole (DAO), Dimethylamino-5-Sulphonic acid, Dipyrromethenboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green-Pyronine Stilbene), Mithramycin, NBD Amine, Nile Red, Nitrobeinzoxadidole, Noradrenaline, Nuclear Fast Red, Nuclear Yellow, Nylosan Brilliant Flavin EBG, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO1, or combinations thereof.

One skilled in the art would certainly know which one to select among such dyes as long as they have appropriate properties such as emission and absorption spectra, hydrophobic or hydrophilic properties, binding to blood proteins and the like.

In some embodiments of the invention the fluorescent dye is Lucifer Yellow CH, and in some embodiments of the invention the fluorescent dye is Indocyanine green.

When the images are acquired by MRI, the detectable tracer is an MRI contrast agent, which can be either a positive or a negative MRI contract agent.

As used herein, "positive MRI contract agent" refers to an agent which increases the signal of the pharmaceutical composition relative to the nearby tissues of fluids, and "negative MRI contract agent" refers to an agent which decreases the signal of the pharmaceutical composition relative to the nearby tissues of fluids.

When the images are acquired by CT, the detectable tracer is a CT contrast agent, such as an Intravascular X-ray contrast agent, that can be introduced into the vasculature of the subject prior to or during the imaging. Intravascular x-ray contrast agents generally opacify the vascular space or extracellular (interstitial) space and are known in the art. Representative examples of CT contrast agents suitable for the present embodiments include, without limitation, ionic and non-ionic iodinated contrast agents (e.g., salts of metrizoic acid, diatrizoic acid, ioversol®, iothalamate sodium and iopamidol). Other contrast agents, such as those described in, e.g., U.S. Pat. Nos. 4,124,705, 5,075,502, 5,141,739, 5,377, 681 and 6,647,283 the contents of which are hereby incorporated by reference, are also contemplated.

Preferably, the method of the present embodiments performs the analysis of the imaging data substantially in real-time. Additionally, the method of the present embodiments provides an analysis report (typically, but not obligatorily in the form of a processed stream of imaging data) substantially in real-time.

As used herein, "real-time" refers to perceived real-time from the point of view of a human observer. In various exemplary embodiments of the invention the analysis of each image of the stream is executed at a sufficiently high speed such that when the stream is displayed to the human observer, e.g., using a display device such as computer screen, the analysis report or results can be displayed contemporaneously therewith and appear continuous to the human. For example, the analysis of images of about 256×256 picture-elements, can be at a rate of at least 10 images per second, or at least 15 images per second, or at least 30 images per second. An update rate of about 30 updates per second corresponds to a standard video frame rate. Thus, in various exemplary embodiments of the invention the method analyzes the stream of imaging data at a video frame rate.

Referring now to the drawings, FIG. 1 is a flowchart diagram describing the method according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more method operations, appearing in the following description or in the flowchart diagrams in a particular order, can be executed in a different order (e.g., a reverse order) or substantially contemporaneously. Additionally, several operations described below are optional and may not be executed.

The method begins at 10 and continues to 11 at which, a vector of features is associated for each picture-element. Various types of features are contemplated. Generally, the features characterize an intensity-time curve, namely, the time-dependence of intensity which is associated with the picture-element. A preferred number of features in the vector is at least 3, or at least 4, or at least 5, or at least 6, or at least 7, or at least 8, or at least 9 or at least 10 features characterizing the time-dependence of the intensity.

A representative example of a grid 20 of picture-elements is illustrated in FIG. 2. The picture-elements of grid 20 is associated with a vector 22 of features, $f_1, f_2, \ldots, f_k$. For clarity of presentation, only one picture-element 24 is shown associated with a vector of features. The skilled artisan would understand that picture-element 24 is a representative picture-element and that many picture-elements, preferably all the picture-element of grid 20, can be associated with vectors.

The resolution characterizing grid 20 and the spatial resolution of the input images can be the same or they can differ. When the resolutions differ, the method preferably comprises a pre-analysis procedure in which the imaging data is adapted to the resolution of grid 20. This can be done by an interpolation technique as known in the art. For example, in some embodiments of the present invention a 2D bicubic interpolation techniques, is employed. This technique is described in Keys, R.G., 1981, "Cubic convolution interpolation for digital image," IEEE transactions on acoustics, speech, and signal processing 29.

In some embodiments of the present invention, at least a few of the features are indicative of temporal intensity variation relative to a baseline intensity. For example, the features may comprise values of intensities along the curve, such as a maximal value relative to a baseline intensity, values at transition points on the curve (one value per transition point) and the like. Generally, a transition point is identified on the curve points in which a functional transition occurs.

As used herein "functional transition" refers to any detectable mathematical transition of a function, including without limitation, a transition of a given function (e.g., a change of a slope, a transition from increment to decrement or vice versa, a transition from a flat behavior to an increasing or decreasing behavior), and a transition from one characteristic functional behavior to another (e.g., a transition from a linear to a nonlinear behavior or a transition from a first nonlinear behavior to a second, different, nonlinear behavior).

The functional transitions can be identified, for example, by calculating a derivative of the time-dependence and finding zeros thereof. As will be appreciated by one of ordinary skill in the art, a transition of a function can be characterized by a zero of one of its derivatives. For example, a transition from increment to decrement or vice versa is characterized by a zero of a first derivative, a transition from a concave region to a convex region or vice versa (points of inflection) is characterized by a zero of a second derivative, etc. According to a preferred embodiment of the present invention any derivative of the time-dependence can be used. Generally, the functional transitions are preferably characterized by a sign inversion of an nth derivative of the time-dependence, where n is a positive integer.

Additionally or alternatively, the functional transitions can be identified by observing deviations from smoothness. In this embodiment, the functional transitions can be identified either with or without calculating the derivatives of the time-dependence. For example, deviations from smoothness can be identified by comparing the time-dependence to a known smooth function.

Another type of features which is contemplated relates to the calculations of time-intervals. For example, a feature can be a time-interval which corresponds to a transition point. Such time-interval can be calculated by subtracting a predetermined reference time from the time corresponding to the particular transition point. The predetermined reference time can be, for example, the time at which the detectable tracer is introduced into the vasculature of the subject. In this embodiment, the method preferably receives the reference time as an input. Also contemplated are features which represent time-intervals between two transition points. Thus, according to some embodiments of the present invention the features comprise at least one interval along the abscissa.

An additional type of features which is contemplated is time-derivative of the time-dependence. Thus, the derivative of the time-dependence can be used both indirectly and directly for extracting features. Indirectly, the derivative is used for identifying transition points at which various features can be obtained or calculated. Directly, the derivative itself is used as a feature. In various exemplary embodiments of the invention the derivative is used in both ways. Firstly, the transition point is identified and secondly the value of the derivative at the identified transition point is stored as one of the features. The time-derivative can be of a first order or of a higher order. A time-derivative of a first order is abbreviated hereinunder as a slope.

The time-derivative is preferably an average time-derivative over a segment at which the intensity curve is monotonic.

The features can also comprise one or more ratios between two values of the intensity. For example, a feature can be extracted by dividing the value of the intensity at one transition point by the value of the intensity at another transition point. Additionally or alternatively, the features can also comprise one or more differences between two values of the intensity. In this embodiment, a feature can be extracted by subtracting the value of the intensity at one transition point from the value of the intensity at another transition point. Thus, according to some embodiments of the present invention the features comprise at least one interval along the ordinate of the intensity curve.

The transition points are preferably extracted from the intensity curve automatically. This can be done using any procedure known in the art. For example, in some embodiments of the present invention the intensity curve is fitted to an analytical function which is preferably segmented into a plurality of segments. It was found by the inventors of the present invention that it is sufficient for the segments to have a linear dependence on time. However, it is not intended to limit the scope of the present invention to any type of function or any number of segments.

FIG. 3 is a schematic illustration of an exemplified intensity-time curve 26. Shown in FIG. 3 are various transition points on curve 26. These include, a reference time-point (R), point of transition from a flat behavior to an increasing behavior (A), point of maximum intensity (B), point of inflection along a segment in which the curve is monotonically decreasing (C) and point of transition from a decreasing behavior to a flat behavior (D). The projections of these points on the time axis (abscissa) are designated as $t_R$, $t_A$, $t_B$, $t_C$ and $t_D$, respectively, and projections of these points on the intensity axis (ordinate) are designated $I_R$, $I_A$, $I_B$, $I_C$ and $I_D$, respectively. Note that in the present example $I_R$ and $I_A$ are approximately the same. The intensity at reference point R can be used as a baseline intensity. At least a few of these points can be used for defining a vector of features. For example, the features can includes intervals such as $t_{RA}=t_A-t_R$, $t_{RB}=t_B-t_R$, $t_{RD}=t_D-t_R$, $t_{AD}=t_D-t_A$ and the like, intensity values or differences between intensity values such as $I_B$, $I_{RB}=I_B-I_R$ and the like, and averaged slopes such as $s_{BR}=(I_B-I_R)/(t_B-t_R)$, $s_{BC}=(I_C-I_B)/(t_C-t_B)$, $s_{DC}=(I_D-I_C)/(t_D-t_C)$, $s_{DB}=(I_D-I_B)/(t_D-t_B)$ and the like.

The features can also comprise combinations (e.g., difference, ratio) of two or more of the aforementioned features.

In some embodiments of the present invention the features comprise a time-interval defined from a time at which the tracer is introduced into vasculature to a time at which the intensity of the respective picture-element rises above the baseline intensity. This feature corresponds, at least approximately, to the aforementioned time-interval $t_{RA}$.

In some embodiments of the present invention the features comprise a time-interval defined from a time at which the tracer is introduced into the vasculature to a time at which the intensity of the respective picture-element reaches the local maximum. This feature corresponds, at least approximately, to the aforementioned time-interval $t_{AB}$.

In some embodiments of the present invention the features comprise a time-interval over which the intensity of the respective picture-element is enhanced relative to baseline intensity. This feature corresponds, at least approximately, to the aforementioned time-interval $t_{AD}$.

In some embodiments of the present invention the features comprise a maximal intensity value over a time-interval over which the intensity of the respective picture-element is enhanced relative to the baseline intensity. This feature corresponds, at least approximately, to the aforementioned intensity value $I_B$.

Thus, at 11 the method provides a plurality of vectors in a multi dimensional feature space. Optionally, the method proceeds to 12 at which the method generates a map of one or more of the features over the grid. The map can be displayed to the user using a display device. Representative examples of such maps are provided in the Examples section that follows (see, e.g., FIGS. 6D-F, 8F, 8G, 9E and 9F).

The method proceeds to 13 at which the picture-elements are clustered according to vectors to provide a plurality of clusters. Any clustering procedure adapted for handling multidimensional data can be used. The present embodiments contemplate hierarchical as well as partitional clustering procedure.

In some embodiments of the present invention a partitional procedure known as K-means is employed. The K-means procedure employs a successive sequence of iterations so as to minimize a predetermined criterion, such as the sum of the squares of the distances from all the data points in the cluster to their nearest cluster centers. The K-means procedure is advantageous because the number of clusters can be determined a priori thereby reducing the complexity of the procedure. In some embodiments of the present invention the K-means procedure is executed for total of two clusters. These embodiments are suitable, for example, for differentiating between picture-element corresponding to blood vessel tissue and picture-element corresponding to extravascular tissue. In some embodiments of the present invention the K-means procedure is executed for total of three clusters. These embodiments are suitable, for example, for differentiating between picture-element corresponding to arterial blood vessel tissue (particularly, but not exclusively, arterioles), picture-element corresponding to venous blood vessel tissue (particularly, but not exclusively, venules) and picture-element corresponding to extravascular tissue.

In some embodiments of the present invention a clustering procedure which is based on graph theory is employed. In these embodiments, each data entry is represented as a vertex on a graph, and similarity measures between data entries are represented as weighted edges between vertices. Clusters are formed by iterative deletions of edges, and by constructing a minimal spanning tree of the graph.

In some embodiments of the present invention a density estimation procedure is employed. In these embodiments, clusters of data are viewed as high density regions separated by low-density regions. An example of a density estimation procedure suitable for the present embodiments is the so called "scale-space clustering" procedure which employs a set of Gaussian kernels as probability distribution functions.

It is expected that during the life of a patent maturing from this application many relevant techniques for clustering multidimensional data will be developed and the scope of the term clustering procedure is intended to include all such new technologies a priori.

Once the clusters are obtained the method proceeds to 14 at which different compartments in the vasculature are identified based on clusters. The identification is according to the characteristic features of each cluster. It was found by the inventors of the present invention that the characteristic features of the clusters can be used for identifying picture-element corresponding to blood vessel tissue and picture-element corresponding to extravascular tissue. Broadly speaking, the change in intensity is typically milder for picture-element corresponding to extravascular tissue than for picture-element corresponding blood vessel tissue.

The present embodiments also contemplate identification of different types of blood vessels, such as arterioles and venules. This can be done, for example, using the features $t_{RA}$, namely the duration from a time at which the tracer is introduced into the vasculature to a time at which intensity rises above the baseline intensity. In some embodiments of the present invention a picture-element is classified as arteriole or venule based on the value of $t_{RA}$. Typically, the value of $t_{RA}$ is lower for picture-elements correspond to arterioles than for picture-elements correspond to venules.

The classification according to $t_{RA}$ can be done over the entire image or region-wise across the image. When the classification is done over the entire image, the association of a picture-element to a vasculature compartment is performed irrespectively of the location of the picture-element within the image.

When the classification is done region-wise, the association of a picture-element to a vasculature compartment is based on the $t_{RA}$ value of the respective picture-element and based on the $t_{RA}$ value of nearby picture-elements, namely picture-element within a radius of R from the respective picture-element. Typical value or R is from 1 picture-element to 50 picture-elements, but values larger than 50 are not excluded from the scope of the present invention. As an example for a region-wise classification, suppose that at region of radius R over the image, the value of $t_{RA}$ is lower for some picture-elements and higher for other picture-elements. In this case, the method can determine that the former picture-elements correspond to arterioles and the latter picture-elements correspond to venules.

In various exemplary embodiments of the invention the method continues to 15 at which the brain functionality of the subject is evaluated based on the clusters. For example, the method can estimate or measure vessels diameter, blood flow (e.g., mean transient time and rCBF), identify changes in diameter (e.g., vasodilatation or constriction) and/or identify vessels permeability.

rCBF can be correlated, for example, to one or more of: the time-interval $t_{RA}$, the intensities $I_B$ and $I_{BR}$ and the slope $s_{AB}$. It was found by the present inventors that at regions in which there is a reduction in $t_{RA}$, and increment in $I_B$ and $s_{AB}$, there is an increased rCBF.

Vasodilatation can be correlated, for example, to one or more of: $t_{RA}$, $t_{AD}$, $I_B$, $I_{BR}$ and $s_{AB}$. It was found by the present inventors that the method can identified vasodilatation when $s_{AB}$ and $I_B$ increase, and $t_{AD}$ decreases at picture-element corresponding to arterioles and venules. Any of these changes can be verified by the method using an appropriate thresholding procedure. In various exemplary embodiments of the invention the method identifies vasodilatation when $s_{AB}$ is increased by approximately 20%, $I_B$ is increased by approximately 2%, and $t_{AD}$ is decreased by approximately 10%.

BBB permeability can be correlated, for example, to one or more of: $t_{RA}$, $t_{AD}$, $I_B$, $I_{BR}$, $s_{AB}$, $s_{BC}$ and $s_{BD}$. It was found by the present inventors that the method can identified BBB permeability when the following criteria are met: (i) at picture-element corresponding to venules, $s_{AB}$ decrease, $I_B$ decreases, and $t_{AD}$ increases; and (ii) at picture-element corresponding to extravascular compartment, $s_{AB}$ decreases, $I_B$ increases, $s_{BD}$ decreases, and $t_{AD}$ increases. These criteria can be accompanied by an appropriate thresholding procedure. In various exemplary embodiments of the invention the method identifies BBB permeability when (i) at picture-element corresponding to venules, $s_{AB}$ decreases by approximately 20%, $I_B$ decreases by approximately 2%, and $t_{AD}$ increases by approximately 10%; and (ii) at picture-element corresponding to extravascular compartment, $s_{AB}$ decreases by approximately 30%, $I_B$ increases by approximately 4%, $s_{BD}$ decreases by approximately 98%, and $t_{AD}$ increases by approximately 175%.

As stated, the present embodiments are also suitable for analyzing imaging data pertaining to blood flow in retinal blood vessels. In the retina of the eye, blood vessels are surrounded by a blood retinal barrier (BRB) exhibiting shared properties with the BBB.

Thus, in various exemplary embodiments of the invention, at 15 the method evaluates the retinal functionality of the subject based on the clusters. For example, the method can identify increased BRB permeability, retinal artery occlusion, retinal venous thrombosis and the like. Employing the technique of the present embodiments to retinal images is advantageous because BRB can serve as a proxy to BBB. Specifically, many pathological conditions such as diabetes mellitus and small vessels disease in ischemic of inflammatory diseases which affect the BRB, also occur in parallel in the BBB. Thus, by analyzing retinal images and assessing BRB permeability, the present embodiments may indicate BBB permeability. In addition, identifying and quantifying blood flow characteristics in one eye have a diagnostic value in the other eye. For example, pathological conditions such as diabetic retinopathy, retinal artery occlusion and age related macular degeneration, which can be identified according to some embodiments of the present invention in one eye can be used as proxies for existence of such conditions in the other eye.

Changes in the retinal blood circulation indicate the extent of various vascular diseases and oftentimes precede the development of functional impairments. The present embodiments can therefore be used for predicting the likelihood of functional impairments in the eyes and indications for treatment.

The method optionally and preferably continues to 16 at which the method issues a report regarding the analysis. The report is typically a graphical output such as an image or a stream of images (e.g., a video stream) that presents the results of the analysis. The graphical output can include one or more maps of the features over the grid, one or more maps of the different vascular or extravascular compartments over the grid.

When the present embodiments are used for analyzing brain images the graphical output can include images pertaining to the functioning of the brain. For example, the graphical output can include an image at which a region in which there is an increased rCBF is highlighted, an image showing vasodilatation, and/or an image showing BBB permeability or highlighting regions of BBB breakdown.

When the present embodiments are used for analyzing retinal images, the report can include images pertaining to the functioning of the retina or the eye. For example, the report can include graphical output such as an image showing retinal artery occlusion, an image showing BBB permeability and/or an image highlighting regions of BRB breakdown.

The report can also include text output describing the results of the analysis. The output can be displayed on a display device such as a computer screen, as known in the art.

The method ends at 17.

Figures 4, 5:
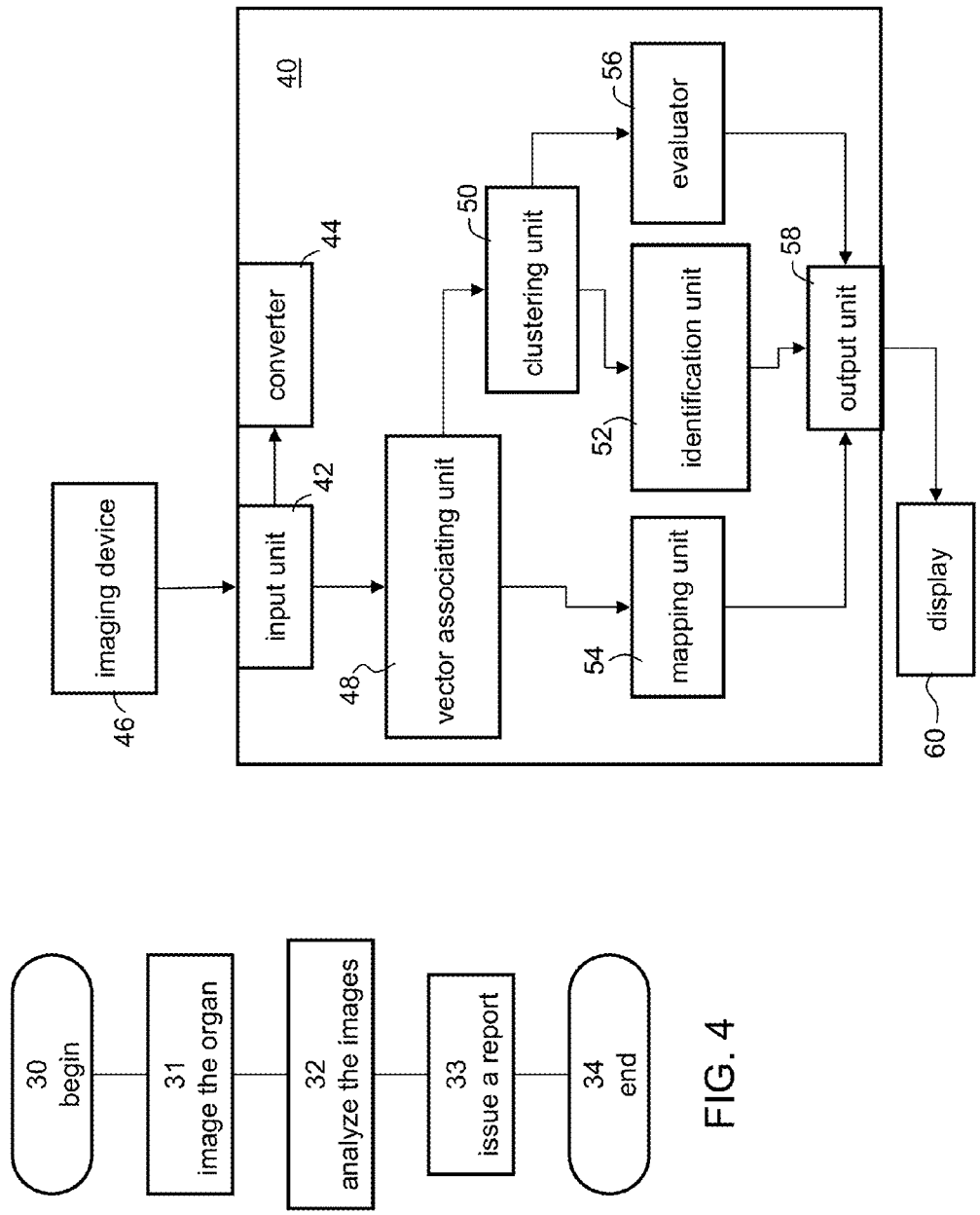

Reference is now made to FIG. 4 which is flowchart diagram describing a method suitable for imaging an organ of a living subject having a detectable tracer in the vasculature, according to various exemplary embodiments of the present invention. The organ of can be any organ, such as, but not limited to, the brain or a retina of the subject. The method begins at 30 and continues to 31 at which the organ is imaged to provide a stream of imaging data. During or shortly before the imaging the detectable tracer is introduced into the vasculature, e.g., by injection. The imaging is preferably florescence imaging, in which case the detectable tracer is a fluorescent dye as further detailed hereinabove. The method continues to 32 at which the stream of imaging data is analyzed. This can be done by execution at least some of the operations described hereinabove and in FIG. 1. The method optionally continues to 33 at which the method issues a report regarding the analysis as further detailed hereinabove.

The method ends at 34.

Reference is now made to FIG. 5 which is a schematic illustration of an Apparatus 40 for analyzing a stream of imaging data, according to various exemplary embodiments of the present invention. The imaging data are arranged gridwise in a plurality of picture-elements associated with intensity values pertaining to a level of a detectable tracer in the vasculature of a living subject, as further detailed hereinabove.

Apparatus 40 may process and analyze the imaging data using the analysis method described above. Apparatus 40 may be or serve as component in a general-purpose computer processor with suitable software for carrying out the operations functions described herein. This software may be downloaded to the processor in electronic form, or it may alternatively be provided on tangible media, such as optical, magnetic or non-volatile electronic memory. Alternatively, Apparatus 40 can be or serve as a component in a special computer processor configured for carrying out the operations described herein. For example, apparatus 40 can be a special computer processor which comprises special firmware embodying computer instructions for carrying out the operations described herein.

In various exemplary embodiments of the invention apparatus 40 comprises an input unit 42 which receives the imaging data in digital or analog form as desired. The imaging data can be provided directly from an imaging device 46. Imaging device 46 can be configured for fluorescent imaging as known in the art. Apparatus 40 can also comprise a converter 44 associated with the input unit, for convert analog signals to digital signals so as to allow the processing to be executed in a digital manner. Apparatus 40 and device 46 can function synchronously as a combined imaging-analysis apparatus.

Apparatus 40 further comprises a vector associating unit 48 which associates, for each picture-element, a vector of features as further detailed hereinabove (see also FIG. 2). Apparatus 40 further comprises a clustering unit 50, which is configured for employing a clustering procedure as further detailed hereinabove. Apparatus 40 can also comprise an identification unit 52 which identifies different compartments in the vasculature based on clusters, as further detailed hereinabove. Unit can also be configured to identify extravascular compartments as further detailed hereinabove.

In various exemplary embodiments of the invention apparatus 40 comprises a mapping unit 54 for generating a map of at least one of features over the grid. In some embodiments of the present invention apparatus 40 comprises an evaluator 56 for evaluating retinal and/or brain functionality based on clusters, as further detailed hereinabove. Apparatus 40 preferably comprises an output unit 58 which issues and outputs to a display device 60 a report regarding the analysis as further detailed hereinabove.

As used herein the term "about" or "approximately" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Brain Imaging

Materials And Methods

All experimental procedures were approved by the Animal Ethics Committee of Ben-Gurion University of the Negev, Beer Sheva, Israel. Chemicals were purchased from Sigma-Aldrich unless otherwise stated.

In-vivo Animal Preparations

In-vivo experiments were performed using established methods (see, e.g., Seiffertet al., 2004, "Lasting blood-brain barrier disruption induces epileptic focus in the rat somatosensory cortex", J. Neurosci. 24, 7829-7836.

Adult male SD rats weighing 200-300 g were deeply anesthetized by intraperitoneal injection of ketamine (100 mg/ml, 0.08 ml/100 g) and xylazine (20 mg/ml, 0.06 ml/100 g). The tail vein was catheterized, and the animal was placed in a stereotactic frame under a florescence stereomicroscope (Zeiss, SteReO Lumar V12). Body temperature was continuously monitored and maintained at 38.0±0.5° C. with a heating pad.

A bone window was drilled over the motor-somatosensory cortex (4 mm caudal, 2 mm frontal, 5 mm lateral to bregma) of one hemisphere. The dura was opened, and the cortex was continuously superfused with artificial cerebrospinal fluid (ACSF) containing (in mM): 129 NaCl, 21 NaHCO$_3$, 1.25 NaH$_2$PO$_4$, 1.8 MgSO$_4$, 1.6 CaCl$_2$, 3 KCl, and 10 glucose (pH 7.4). To induce increased rCBF, the intraorbital ethmoidal nerve, including the parasympathetic nerve fibers from the spheno-palatine ganglion (SPG) was isolated (for further details of such technique see, e.g., Henninger N and Fisher M., 2007, "Stimulating circle of Willis nerve fibers preserves the diffusion-perfusion mismatch in experimental stroke," Stroke 38, 2779-2786) and stimulated (NeuroPath™, BrainsGate) by two sets of 60 s of stimulation separated by an interval of 12 s (10 Hz, square pulse width 500 μs, 1-6 mA).

For disruption of the BBB, bile salt deoxycholic acid (DOC) was added to the ACSF (2 mM), and the cortex was perfused for 30 min.

To induce focal ischemia, a photochemical agent Rose bengal (RBG; 7.5 mg/ml, in saline) was injected (0.133 ml/100 g body weight) via intravascular injection.

The exposed cortex was then illuminated with a halogen light, transferred through fiber optic bundles (Zeiss, KL 1500 LCD). To confirm the generation of an infarct, after the experiment the bone window was carefully closed, the animal was sutured and put back in cage for recovery. Two to three weeks later, the brain was fixed by transcardial perfusion using 4% paraformaldehyde (PFA), removed and stored for 48 hours in PFA. 40 μm coronal sections were mounted and stained using cresyl violet.

In some experiments, animals were injected with the BBB-non-permeable albumin-binding dye Evans blue for confirmation of BBB breakdown.

For method validation, in some experiments the rCBF was monitored with a laser Doppler flowmeter (LDF) (Oxford Optronix, OxyFlo™ 2000). Changes in the rCBF were calculated as percent change from the averaged baseline signal recorded for 30 min prior to treatment.

Real-time Florescence Imaging

For imaging rCBF and BBB permeability, a non-permeable florescent dye, Lucifer yellow CH dipotassium salt (LY, FW=521.58) or FITC-labeled serum albumin were injected intravenously. Full-resolution (658×496) images of cortical surface vessels were obtained at a rate of 12-30 images per second using an EMCCD camera (DL-658M-TIL, Andor Technology PLC.) before, during, and after injection of the tracer (total of 20-40 seconds). About 15-20 minutes after LY injection, averaged image intensity returned to pre-injection values, and the injection was repeated.

Image Analysis

To reduce memory usage and computation time, images were rescaled (to 256×256) using a 2D bicubic interpolation technique.

Sub-pixel image registration to overcome artifacts due to small movements was performed by applying to each image a single step discrete Fourier transform such as the transform described in Guizar-Sicairos et al., 2008, "Efficient subpixel image registration algorithms," Optical Letters 33, 156-158. To increase the signal-to-noise ratio, each frame was registered according to a moving average of several preceding images.

Signal intensity changes over time and space were analyzed. Each pixel was represented by a vector of features which was extracted from the intensity-time curve. Cluster analysis was then performed using a K-means clustering algorithm as known in the art (see, e.g., Hartigan, A., Wong, M. A., 1979, "A K-Means Clustering Algorithm," Applied Statistics 28, 100-108) so as to separate between signal behavior in arteries, veins and the extravascular matrix.

The injection time of the tracer was used as a reference time and defined as "t=0". The following features were used for the clustering process: baseline, representing the background intensity ("noise") before injection of the tracer (0-2.5 s, about 30-50 images), time to the first detection of a significant increase in intensity compared to the baseline (referred to herein as "time to incline" and denoted tti), maximal value (denoted max), slope of the signal intensity increase between tti and max (denoted incline), time from t=0 to maximal intensity (denoted ttmax), slope of the signal intensity decrease (denoted decline), and time from the tracer injection to the time at which the rapid decline terminated (referred to herein as "time to decline" and denoted ttd). Note that these features correspond to the features described above with reference to FIG. 3. Specifically, baseline corresponds to $I_R$, tti corresponds to the $t_{AR}$, max corresponds to $I_B$, incline corresponds to $S_{BR}$, ttmax corresponds to $t_{BR}$, decline corresponds to $s_{DB}$, and ttd corresponds to $t_{RC}$.

Automatic feature extraction from the intensity-time curve was performed by least-square errors fitting of the measured signal intensity curve to a segmented linear model with four segments. The model included five breakpoints: two fixed breakpoints at the start and end points, one fixed internal breakpoints at the time to maximal intensity, and two internal breakpoints at the time to incline and time to decline. The latter were used as degrees of freedom for the least-square errors fitting procedure.

tti was obtained by identifying a point at which the segmented linear model first exhibited a positive slope (see point A in FIG. 3) and measuring the time from t=0 to this point.

Incline was calculated as the averaged slope of the line connecting the max value to the preceding baseline. Decline was calculated as the averaged slope from max to ttd. Additionally, a mean transient time was calculated for each pixel. This calculation was under the assumption that on the average, the MTT of all particles is the same and behaves approximately as a first-in-first-out sequence. Let the times in which the first particle enters and leaves the system be $t_{enter}$ and $t_{exit}$ respectively. Assuming all particles, entering the system also exit, the number of particles entering the system between $t_{enter}$ and $t_{exit}$ equals the amount of particles leaving the system after $t_{exit}$. Accordingly, $t_{exit}$ is the time instance which divides the total area under the intensity curve into two equal areas. Since $t_{enter}$ equals tti, MTT was therefore defined as MTT=$t_{exit}$-$t_{enter}$. Alternatively, MTT can be defined as the difference between ttd and tti (MTT=ttd−tti).

The number of clusters found to describe arterioles and venules were summed together as the cerebral vascular area (CBA).

Results

Visualization of Flow and Dynamic Image Analysis

FIGS. 6A-I show flow visualization in pial vessels and the process of image analysis.

FIGS. 6A and 6B show florescence images of the vessels 5.15 seconds (FIG. 6A) and 6.85 seconds (FIG. 6B) following the injection of the fluorescent tracer.

FIG. 6C shows intensity-time curve created by the image analysis procedure of the present embodiments. The inset of FIG. 6C shows the segmented linear model (red) and the raw data (blue).

FIGS. 6D-F show the image analysis procedure, specifically maps of tti, incline and max.

FIGS. 6G-I show the cluster analysis procedure. FIG. 6G depicts the result of selecting the number of clusters to be 2, marking presumed blood vessels in red and extravascular tissue in gray. FIG. 6H depicts the result of selecting the number of clusters to be 3, marking arterioles in red, venules in blue and tissue in gray. FIG. 6-I shows the intensity as a function of the time after the identification of arteries, veins and extravascular tissue.

On average, 5.15±0.15 seconds after injection, the tracer was detected in the pial arterioles (FIG. 6A), followed by delayed (6.85±0.30 seconds) labeling of the venules (FIG. 6B). Image analysis revealed a rapid increase, followed by a slower decrease in the intensity of the fluorescent signal, which reflected the flow of tracer through the local vasculature (FIG. 6C).

Several physiologically relevant features were measured: baseline, representing the background intensity ("noise") before injection of the tracer (0-2.5 seconds, about 30-50 images); tti, which was shorter for vessels identified anatomically as arterioles than for venules in the same region (FIGS. 6A and 6D); incline (FIG. 6E); max (FIG. 6F); and ttd (not shown).

Pixel-wise analysis maps created for each of the features demonstrated differences between anatomically defined arterioles, venules and extravascular brain tissue (the latter showing, a significantly smaller change in fluorescent intensity). Cluster analysis using the measured parameters allowed automatic separation, depending on the selected number of clusters n. For n=2, a clear separation was observed between blood vessels and the extravascular tissue (FIG. 6G), for n=3 a clear separation was observed between anatomically defined arterioles and venules (FIG. 6H).

Imaging of Increased rCBF

The extent to which the technique of the present embodiments is sensitive for the detection of physiological and pathological changes in the rCBF was also explored. This was done by stimulating the ethmoidal nerve so as to increase rCBF in the ipsilateral fronto-parietal cortex FIGS. 7A-H show the results of CBF increase following stimulation of the ethmoidal nerve.

FIGS. 7A and 7B show images during injection of the fluorescent tracer under control conditions (FIG. 7A) and at the end of each 3 mA stimulus train (FIG. 7B). The images demonstrate vasodilatation of surface vessels. FIG. 7C is a graph showing mean measurements of maximal rCBF increase during each stimulation train, and the inset shows the results of monitoring by laser Doppler flowmeter. An increased rCBF was observed in each stimulation train above 1 mA. Repeated stimulation of the nerve by pulses greater than 1 mA consistently resulted in a variable, but significant, increase in vessel diameter and in the averaged rCBF measured with the laser Doppler flowmeter (n=5). In a different set of experiments, trains of 60 s of stimulation separated by 12-s intervals (500 μs duration, 10 Hz, 1-6 mA) were given every 15 min with increasing stimulation intensity. LY was injected i.v. at the end of each train.

FIG. 7D is a histogram showing induced increase in rCBF as a result of the stimulation of the ethmoidal nerve. A clear increase in vessel diameters was observed with a stimulation intensity above 1 mA (see also FIG. 7B). Vasodilatation was greater for arterioles than for venules (data not shown).

FIGS. 7E and 7F show the results of dynamic analysis, specifically the max parameter which correlates to flow, during tracer injection under control conditions (FIG. 7E) and at the end of each 3 mA stimulus train (FIG. 7F). An increasing change in the maximal intensity following stimulation was observed. FIGS. 7G and 7H show the mean intensity changes during injection in the arterial (7G) and venous compartments (7H). Note that a significant reduction in tti and increases in incline and max values were observed at stimulation intensities higher than 1 mA. Both arterial and venous compartments showed similar responses, suggesting increased rCBF and drainage (outflow).

Imaging of BBB Breakdown

Under conditions in which the BBB is disrupted, the impermeable tracer diffuses out of the blood vessels and increases the image intensity in the extravascular compartment.

FIGS. 8A-H shows the results of analysis for the detection of BBB permeability.

FIGS. 8A and 8B are fluorescent images of surface vessels during the venous phase of injection behavior before (FIG. 8A) and after (FIG. 8B) exposing the brain to DOC. 30 min after brain exposure to DOC, repeating tracer injection showed clear staining of the extravascular tissue indicating BBB breakdown.

FIG. 8C shows a coronal section following treatment with DOC and injection of Evans blue. Extravasation of the Evans-blue-albumin complex into the treated cortical tissue indicated BBB breakdown, confirming the fluorescent imaging findings.

FIG. 8D shows results of monitoring by laser Doppler flowmeter, and FIG. 8E is a histogram showing the number of pixels in the arterial and venous clusters under control conditions (ACSF) and following perfusion with DOC as determined by the image analysis of the present embodiments. The laser Doppler flowmeter measurements (FIG. 8D) demonstrated a steady and consistent increase in rCBF in all experiments (n=5). The increased rCBF was associated with vasodilatation of both arterioles and venules, as confirmed by the image analysis of the present embodiments which detected increased CBA of both the arterial and venous clusters following DOC (FIG. 8E).

FIGS. 8F and 8G are maps of the MTT parameter as calculated according to some embodiments of the present invention under control conditions (FIG. 8F) and following perfusion with DOC (FIG. 8G). Decreased MTT was observed in arterioles and robust increase was observed in the extravascular space where the tracer was accumulating.

Vasodilatation was associated with increased incline and max values and a decrease in MTT value (p<0.0001), consistent with increased rCBF. The changes in incline, max and MTT at pixels corresponding to arterioles and venules are summarized in table 1 below

TABLE 1

| Following DOC | Control | Parameter |
|---|---|---|
| 6.79 ± 3.6 units per second | 5.4 ± 2 units per second | incline |
| 606.3 ± 27 | 594.1 ± 11.08 units | max |
| 3.33 ± 0.9 seconds | 3.85 ± 0.72 seconds | MTT |

FIG. 8H shows intensity curves for the arterial, venous, and extravascular compartments. As shown, an increased flow in the arterial compartment and decreased signal intensity in the venous compartment were observed after DOC (dotted line). Table 2 below summarizes the obtained values of the incline, max and MTT parameters at pixels corresponding to venules. The table demonstrates a decrement in incline and max and increment in MTT ($p \ll 0.001$).

TABLE 2

| Following DOC | Control | Parameter |
|---|---|---|
| 3.07 ± 1.5 units per second | 3.81 ± 1.3 units per second | incline |
| 572 ± 7.3 | 588.57 ± 8 units | max |
| 4.74 ± 1.41 seconds | 4.26 ± 0.79 seconds | MTT |

A robust slowing of the signal decay in the extravascular compartment after BBB breakdown was also observed. The obtained values of the incline, max, decline and MTT parameters for the extravascular compartment are summarized Table 3. The table demonstrates decrease in incline and decline, and an increase in max and MTT ($p < 0.001$).

TABLE 3

| Following DOC | | Control | | Parameter |
|---|---|---|---|---|
| 2.5 ± 2 | units per second | 3.25 ± 2 | units per second | incline |
| 590.18 ± 13.14 | units | 568.18 ± 11.27 | units | max |
| 0.05 ± 0.1 | units per second | 2.84 ± 4.3 | units per second | decline |
| 10.88 ± 6.18 | seconds | 3.9 ± 0.87 | seconds | MTT |

This experiment demonstrated that DOC induced vasodilatation, increased flow in brain arterioles and accumulation of tracer in the extravascular space, lead to a decreased signal in the venous compartment.

Imaging Blood Flow in Focal Ischemia

The RBG model was used to induce focal intravascular thrombosis. The results are shown in FIGS. 9A-I.

Figure 9C:
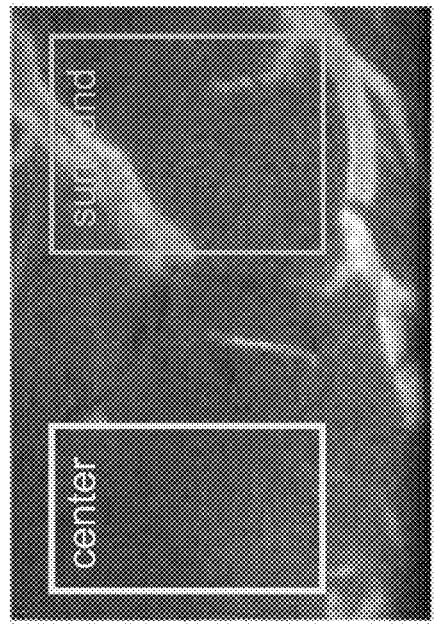
Figure 9D:
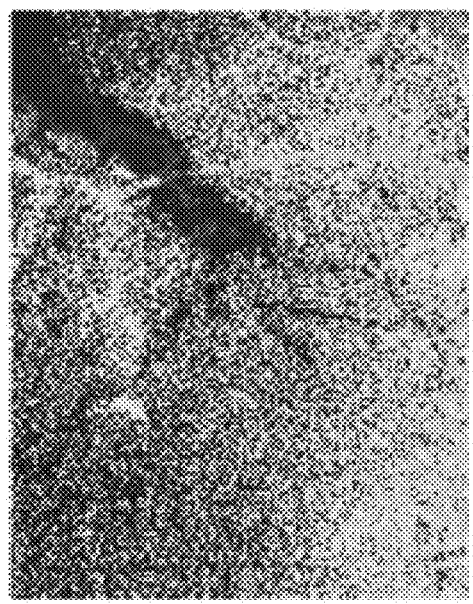

FIGS. 9A-D are fluorescent images of the arterial (FIGS. 9A and 9C) and venous (FIGS. 9B and 9D) compartments before (FIGS. 9A and 9B) and 30 min after (FIGS. 9C and 9D) i.v. injection of RBG and cortical exposure to halogen light. FIGS. 9A-D are snapshots of series of images forming video streams. FIGS. 9A and 9C are snapshots corresponding to t=6 s, FIG. 9B is a snapshot corresponding to t=10.8 s, and FIG. 9D is a snapshot corresponding to t=11.6 s. The rectangles in FIGS. 9C and 9D mark regions of thrombotic vessels (left rectangle) and intact vessels (right rectangle). These regions are referred to herein as "center" and "surround", respectively.

Figure 9E:
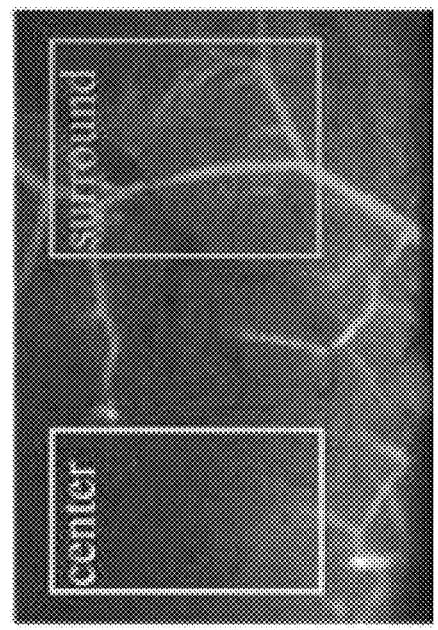
Figure 9F:
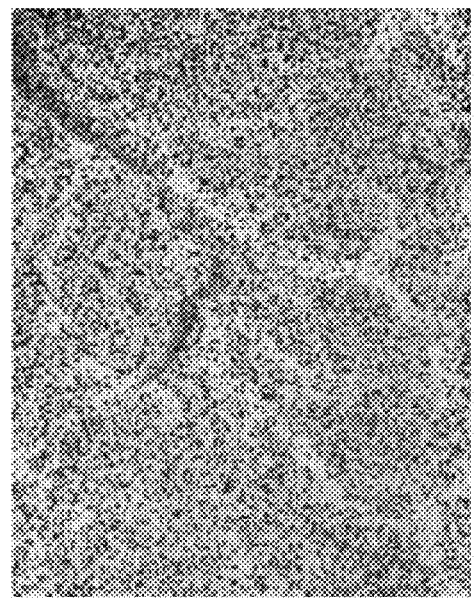

FIGS. 9E and 9F are MTT maps before (FIG. 9E) and after (FIG. 9F) i.v. injection of RBG and cortical exposure to halogen light.

FIG. 9G is an image showing coronal section 30 minutes after Evans-blue-albumin complex injection (1 hour after RBG treatment), and FIG. 9H is an image showing histological brain section (cresyl violet staining) 21 days after a phothrombotic leasion coronal section.

FIG. 9-I shows intensity curve for the arterial, venous and extravascular compartments, for the center and surround regions. In FIG. 9-I, solid lines are intensity curves before RBG injection (control) and dotted lines are intensity curves after RBG injection (treated).

As shown, 30 minutes after RBG injection and exposure to light, LY injection demonstrated a clear reduction in rCBF in the region of the cortex exposed to light (center region). On the other hand, the blood supply in the surrounding brain tissue (surround region) was intact with evidence for a mild enhancement in rCBF and BBB permeability.

Image intensity in both the arterial and venous compartments in the center region showed a significant reduction in the signal to the level of the "background" extravascular compartments. In the surround region, a clear increase in signal was observed in the arterial and venous compartments (see FIG. 9-I, dotted line).

Increased incline, max and MTT values were observed in the surround region for both arterial and venous compartments (see FIGS. 9E-I). Note that the extravascular compartment showed a similar incline and max value but increased MTT with a robust slowing of the decline phase, similar to that observed when the BBB was disrupted (see FIGS. 8F and 8G). This finding was supported by extravasation of the Evans-blue-albumin complex into the brain tissue surrounding the treated cortex (see FIG. 9G).

Example 2

Retinal Imaging

A male human volunteer, age 25 was injected intravenously with fluorescent tracer sodium fluorescein (McCarthy's Limited, Essex, UK), a crystalline hydrocarbon with a molecular weight of 376 daltons. The tracer was injected into a peripheral vein using a standard intravenous catheter as routinely used in the eye clinic. Retinal images, at a resolution of 640×480 DPI of the volunteer's right retina were captured using an SLO camera (NIDEK Co., LTD.), at a rate of 25 frames per second during the injection of the tracer (total of 60 seconds).

Several preprocessing procedures were employed. These include, image rescaling to 256×256 using a 2D bicubic interpolation technique, and movement correction using a single step discrete Fourier transform as described in Example 1 above. Image analysis and clustering were as described in Example 1 above.

FIG. 10 shows a representative example of a fluorescence image.

FIGS. 11A and 11B show the cluster analysis procedure. FIG. 11A depicts the arterial compartment (red), venous compartment (blue) and retinal tissue (gray). FIG. 11B shows the intensity as a function of the time in arbitrary units after the identification of arteries, veins and extravascular tissue.

Example 3

Human Brain Imaging

Video images of human brain were captured during a neurosurgical procedure and were obtained with the courtesy of Dr. Johannes Woitzik of University Hospital Mannheim. The human subject was a 41 year old woman experiencing left hemispheric malignant stroke. For description of the neurosurgical procedure, please see Woitzik et al., "Cortical Perfusion Measurement by Indocyanine-Green Videoangiography in Patients Undergoing Hemicraniectomy for Malignant Stroke," Stroke (2006), 37:1549-1551. Indocyanine green was injected into a peripheral vein (0.3 mg/Kg body weight), and the fluorescence signal was recorded by a video camera at a rate of 25 frames per second. Preprocessing, image analysis and clustering was performed as described in Example 1 above on the original frames.

FIGS. 12A and 12B are examples of frames captured during the neurosurgical procedure, where FIG. 12A corresponds to the arterial phase and FIG. 12B corresponds to the venous phase.

FIG. 12C shows the intensity in arbitrary units as a function of the time after cluster analysis and identification of arteries, veins and extravascular tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of analyzing a stream of imaging data arranged gridwise in a plurality of picture-elements associated with intensity values pertaining to a level of a detectable tracer in the vasculature of a living subject, the method comprising:
   for each picture-element, associating a vector of features indicative of temporal intensity variation relative to a baseline intensity, thereby providing a plurality of vectors, wherein said features comprise a time-interval defined from a time at which said tracer is introduced into said vasculature to a time at which intensity of said picture-element reaches a local maximum;
   clustering the picture-elements according to said vectors, thereby providing a plurality of clusters; and
   identifying different compartments in the vasculature based on said clusters.

2. A method of imaging an organ of a living subject having a detectable tracer in the vasculature, comprising:
   imaging the organ to provide a stream of imaging data; and
   executing the method of claim 1.

3. The method according to claim 2, wherein said imaging comprises fluorescence imaging.

4. The method according to claim 2, wherein said imaging comprises computerized tomography.

5. The method according to claim 2, wherein said imaging comprises magnetic resonance imaging.

6. The method according to claim 1, further comprising identifying at least one extravascular compartment based on said clusters.

7. The method according to claim 1, further comprising generating a map of at least one of said features over the grid.

8. The method according to claim 1, wherein the imaging data pertain to a retina of the subject.

9. The method according to claim 8, further comprising evaluating retinal functionality based on said clusters.

10. The method according to claim 1, wherein the imaging data pertain to the brain of the subject.

11. The method according to claim 10, further comprising evaluating brain functionality based on said clusters.

12. An apparatus for analyzing a stream of imaging data arranged gridwise in a plurality of picture-elements associated with intensity values pertaining to a level of a detectable tracer in the vasculature of a living subject, the apparatus comprising:
   a vector associating unit having a circuit for associating, for each picture-element, a vector of features indicative of temporal intensity variation relative to a baseline intensity, thereby to provide a plurality of vectors, wherein said features comprise a time-interval defined from a time at which said tracer is into said vasculature to a time at which intensity of said picture-element reaches a local maximum;
   a clustering unit having a circuit for clustering the picture-elements according to said vectors, thereby to provide a plurality of clusters; and
   an identification unit having a circuit for identifying different compartments in the vasculature based on said clusters.

13. An imaging apparatus, comprising an imaging device and the apparatus of claim 12.

14. The apparatus according to claim 12, wherein said identification unit is configured for identifying at least one extravascular compartment based on said clusters.

15. The apparatus according to claim 12, further comprising a mapping unit having a circuit for generating a map of at least one of said features over the grid.

16. The apparatus according to claim 12, wherein the imaging data pertain to a retina of the subject.

17. The apparatus according to claim 16, further comprising an evaluator for evaluating retinal functionality based on said clusters.

18. The method according to claim 9, wherein said retinal functionality comprises blood retinal barrier permeability.

19. The method according to claim 9, wherein said retinal functionality comprises retinal artery occlusion.

20. The apparatus according to claim 12, wherein the imaging data pertain to the brain of the subject.

21. The apparatus according to claim 20, further comprising an evaluator for evaluating brain functionality based on said clusters.

22. The method according to claim 11, wherein said brain functionality comprises regional cerebral blood flow.

23. The method according to claim 11, wherein said brain functionality comprises vasodilatation.

24. The method according to claim 11, wherein said brain functionality comprises blood brain barrier permeability.

25. The method according to claim 1, wherein said features comprise time-intervals measured from a reference time to a time at which said intensity exhibits a functional transition.

26. The method according to claim 1, wherein said features comprise a time-interval defined from a time at which said tracer is introduced into said vasculature to a time at which intensity of said picture-element rises above said baseline intensity.

27. The method according to claim 1, wherein said features comprise a time-interval over which said intensity of said picture-element is enhanced relative to said baseline intensity.

28. The method according to claim 1, wherein said features comprise a combination of at least two time-intervals selected from the group consisting of:

a time-interval defined from a time at which said tracer is introduced into said vasculature to a time at which intensity of said picture-element rises above said baseline intensity;

a time-interval over which said intensity of said picture-element is enhanced relative to said baseline intensity; and a time-interval defined from said time at which said tracer is introduced into said vasculature to a time at which intensity of said picture-element reaches a local maximum.

29. The method according to claim 1, wherein said features comprise a maximal intensity value over a time-interval over which said intensity of said picture-element is enhanced relative to said baseline intensity.

30. The method according to claim 1, wherein said features comprise at least one slope characterizing rate of change in intensity of said picture-element.

31. The method according to claim 1, wherein said features comprise a time-interval defined from a time at which said tracer is introduced into said vasculature to a time at which intensity of said picture-element rises above said baseline intensity, and wherein said picture-element is classified as arteriole or venule based said time-interval and respective time-intervals of nearby picture-elements.

32. A method of analyzing a stream of imaging data arranged gridwise in a plurality of picture-elements associated with intensity values pertaining to a level of a detectable tracer in the vasculature of a living subject, the method comprising:

for each picture-element, associating a vector of features indicative of temporal intensity variation relative to a baseline intensity, thereby providing a plurality of vectors;

clustering the picture-elements according to said vectors, thereby providing a plurality of clusters; and identifying different compartments in the vasculature based on said clusters;

wherein said features comprise at least one of:

a time-interval defined from a time at which said tracer is introduced into said vasculature to a time at which intensity of said picture-element rises above said baseline intensity;

a time-interval over which said intensity of said picture-element is enhanced relative to said baseline intensity;

a time-interval defined from said time at which said tracer is introduced into said vasculature to a time at which intensity of said picture-element reaches a local maximum;

a maximal intensity value over a time-interval over which said intensity of said picture-element is enhanced relative to said baseline intensity; and a slope characterizing rate of change in intensity of said picture-element.

33. A method of analyzing a stream of imaging data arranged gridwise in a plurality of picture-elements associated with intensity values pertaining to a level of a detectable tracer in the vasculature of a living subject, the method comprising:

for each picture-element, associating a vector of features indicative of temporal intensity variation relative to a baseline intensity, thereby providing a plurality of vectors;

clustering the picture-elements according to said vectors, thereby providing a plurality of clusters; and identifying different compartments in the vasculature based on said clusters;

wherein the imaging data pertain to a retina of the subject.

34. The method according to claim 33, further comprising evaluating retinal functionality based on said clusters.

35. The method according to claim 34, wherein said retinal functionality comprises a functionality selected from the group consisting of blood retinal barrier permeability, and retinal artery occlusion.

36. An apparatus for analyzing a stream of imaging data arranged gridwise in a plurality of picture-elements associated with intensity values pertaining to a level of a detectable tracer in the vasculature of a living subject, the apparatus comprising:

a vector associating unit having a circuit for associating, for each picture-element, a vector of features indicative of temporal intensity variation relative to a baseline intensity, thereby to provide a plurality of vectors;

a clustering unit having a circuit for clustering the picture-elements according to said vectors, thereby to provide a plurality of clusters; and an identification unit having a circuit for identifying different compartments in the vasculature based on said clusters;

wherein the imaging data pertain to a retina of the subject.

37. A method of analyzing a stream of imaging data arranged gridwise in a plurality of picture-elements associated with intensity values pertaining to a level of a detectable tracer in the vasculature of a living subject, the method comprising:

for each picture-element, associating a vector of features indicative of temporal intensity variation relative to a baseline intensity, thereby providing a plurality of vectors;

clustering the picture-elements according to said vectors, thereby providing a plurality of clusters; and identifying different compartments in the vasculature based on said clusters;

wherein said features comprise a maximal intensity value over a time-interval over which said intensity of said picture-element is enhanced relative to said baseline intensity.

38. A method of analyzing a stream of imaging data arranged gridwise in a plurality of picture-elements associated with intensity values pertaining to a level of a detectable tracer in the vasculature of a living subject, the method comprising:

for each picture-element, associating a vector of features indicative of temporal intensity variation relative to a baseline intensity, thereby providing a plurality of vectors, wherein said features comprise at least one slope characterizing rate of change in intensity of said picture-element;

clustering the picture-elements according to said vectors, thereby providing a plurality of clusters; and identifying different compartments in the vasculature based on said clusters.

39. A method of analyzing a stream of imaging data arranged gridwise in a plurality of picture-elements associated with intensity values pertaining to a level of a detectable tracer in the vasculature of a living subject, the method comprising:

for each picture-element, associating a vector of features indicative of temporal intensity variation relative to a baseline intensity, thereby providing a plurality of vectors, wherein said features comprise a time-interval defined from a time at which said tracer is introduced into said vasculature to a time at which intensity of said picture-element rises above said baseline intensity, and wherein said picture-element is classified as arteriole or venule based said time-interval and respective time-intervals of nearby picture-elements;

clustering the picture-elements according to said vectors, thereby providing a plurality of clusters; and identifying different compartments in the vasculature based on said clusters.

\* \* \* \* \*